(12) United States Patent
Daniloff et al.

(10) Patent No.: US 7,078,554 B2
(45) Date of Patent: Jul. 18, 2006

(54) DETECTION OF GLUCOSE IN SOLUTIONS ALSO CONTAINING AN ALPHA-HYDROXY ACID OR A BETA-DIKETONE

(75) Inventors: George Y. Daniloff, Mountain View, CA (US); Aristotle G. Kalivretenos, Columbia, MD (US); Alexandre V. Nikolaitchik, Frederick, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 0 days.

(21) Appl. No.: 10/956,133

(22) Filed: Oct. 4, 2004

(65) Prior Publication Data

US 2005/0043275 A1  Feb. 24, 2005

Related U.S. Application Data

(60) Division of application No. 10/187,903, filed on Jul. 3, 2002, now Pat. No. 6,800,451, which is a continuation-in-part of application No. 10/029,184, filed on Dec. 28, 2001, now abandoned, which is a continuation-in-part of application No. 09/754,217, filed on Jan. 5, 2001, now abandoned.

(60) Provisional application No. 60/363,885, filed on Mar. 14, 2002, provisional application No. 60/329,746, filed on Oct. 18, 2001, provisional application No. 60/269,887, filed on Feb. 21, 2001.

(51) Int. Cl.
C07F 5/04 (2006.01)
C07F 5/02 (2006.01)

(52) U.S. Cl. .......................... 558/288; 564/8
(58) Field of Classification Search ................ 558/228; 564/8
See application file for complete search history.

(56) References Cited

U.S. PATENT DOCUMENTS

| | | | |
|---|---|---|---|
| 5,503,770 A | 4/1996 | James et al. | |
| 5,516,645 A | 5/1996 | Daniel et al. | |
| 5,998,594 A | 12/1999 | Goodman et al. | |
| 6,063,637 A | 5/2000 | Arnold et al. | |
| 6,344,360 B1 | 2/2002 | Colvin et al. | |
| 6,366,793 B1 | 4/2002 | Bell et al. | |
| 6,511,814 B1 | 1/2003 | Carpenter | |

FOREIGN PATENT DOCUMENTS

EP   0 729 962 A1   9/1996

OTHER PUBLICATIONS

James, et al. "Novel Saccharide-Photoinduced Electron Transfer Sensors Based on the Interaction of Boronic Acid and Amine" J. Am. Chem. Soc , 1995, 8982-8987.*

James, Tony D. et al. *A glucose-specific molecular fluorescence sensor*. Angewandte Chemie (1994), 106(21), 2287-9, XP002222904.

Bielecki, Mia et al. *A fluorescent glucose sensor binding covalently to all five hydroxy group of .alpha.—D-glucofuranose. A reinvestigation*. Journal of the Chemical Society, Perkin Transactions 2: Physical Organic Chemistry (1999), (3), 449-455, XP002222905.

Sandanayake, K.R.A. Samankumara et al. *Molecular design of sugar recognition systems by sugar-diboronic acid macrocyclization*. Pure and Applied Chemistry (1996), 68(6), 1207-1212, XP002222906.

Arimori, S., *Sugar Sensing by Chiral Orientation of Dimeric Boronic Acid Appended Porphyrins Which Show Selectivity for Glucose and Xylose*. Chemistry Letters (1996), vol. 1, 77-8.

DiCesare N., *Evaluation of Two Synthetic Glucose Probes for Fluorescence Lifetime Based Sensing*, Analytical Biochemistry (2001), 294(2)154-60.

Daniloff, G., *Continuous Glucose Monitoring: Long Term Implantable Sensor Approach*. Diabetes Technology & Therapeutics (1999), 1(3)261-6.

Shinkai, S., *Molecular Design of Artificial Sugar Sensing Systems*, Trends in Analytical Chemistry (1996), 15(5)188-94.

* cited by examiner

Primary Examiner—Joseph K. McKane
Assistant Examiner—Joseph R. Kosack
(74) Attorney, Agent, or Firm—Rothwell, Figg, Ernst & Manbeck PC

(57) ABSTRACT

Compositions and methods for determining the presence or concentration of glucose in a sample which may also contain an alpha-hydroxy acid or a beta-diketone. The method uses a compound having at least two recognition elements for glucose, oriented such that the interaction between the compound and glucose is more stable than the interaction between the compound and the alpha-hydroxy acid or beta-diketone, such that the presence of the alpha-hydroxy acid or the beta-diketone does not substantially interfere with said determination.

5 Claims, 16 Drawing Sheets

DETECTION OF GLUCOSE IN SOLUTIONS ALSO CONTAINING AN ALPHA-HYDROXY ACID OR A BETA-DIKETONE

CROSS-REFERENCE TO RELATED APPLICATIONS

The present application is a divisional of application Ser. No. 10/187,903 filed Jul. 3, 2002 now U.S. Pat. No. 6,800,451, which is a continuation-in-part of application Ser. No. 10/029,184 filed Dec. 28, 2001 now abandoned, which is a continuation-in-part of application Ser. No. 09/754,217 filed Jan. 5, 2001 now abandoned and claims the benefit of application Ser. No. 60/363,885 filed Mar. 14, 2002, application Ser. No. 60/329,746 filed Oct. 18, 2001 and application Ser. No. 60/269,887 filed Feb. 21, 2001.

STATEMENT REGARDING FEDERALLY SPONSORED RESEARCH OR DEVELOPMENT

Not applicable.

BACKGROUND OF THE INVENTION

1. Field of the Invention

The present invention relates to the detection of glucose in samples which may also contain potential interfering compounds, such as α-hydroxy acids or β-diketones.

2. Description of the Related Art

The complexation of carbohydrates, including glucose, with phenylboronic acid has been known for a long time and the reversibility of that interaction has served as a basis for the chromatographic separation of sugars. Specifically, in 1959, Lorand and Edwards reported association constants for aqueous associations of phenylboronic acid with many saturated polyols; binding interactions ranged from very weak (e.g., ethylene glycol, $K_d$=360 mM) to moderately strong (e.g., glucose, $K_d$=9.1 mM). See J. Yoon, et al., *Bioorganic and Medicinal Chemistry* 1 (4):267–71 (1993). The binding mechanism is believed to occur through bonding of adjacent hydroxyl groups on glucose to hydroxyl groups on a boronate moiety.

U.S. Pat. No. 5,503,770 (James, et al.) describes a fluorescent boronic acid-containing compound that emits fluorescence of a high intensity upon binding to saccharides, including glucose. The fluorescent compound has a molecular structure comprising a fluorophore, at least one phenylboronic acid moiety and at least one amine-providing nitrogen atom where the nitrogen atom is disposed in the vicinity of the phenylboronic acid moiety so as to interact intramolecularly with the boronic acid. Such interaction thereby causes the compound to emit fluorescence upon saccharide binding. See also T. James, et al., *J. Am. Chem. Soc.* 117 (35):8982–87 (1995).

Additionally, fluorescent sensors using an anthrylboronic acid-containing compound for detecting blood glucose are known in the art. For example, J. Yoon, et al., *J. Am. Chem. Soc.* 114:5874–5875 (1992) describe that anthrylboronic acid can be used as a fluorescent chemosensor for signaling carbohydrate binding, including binding of glucose and fructose.

Unfortunately, compounds which interact with glucose in the manner described above also have a tendency to interact with other compounds having hydroxyl groups, thus reducing the specificity of a glucose assay, especially when assaying physiological samples which may contain interfering amounts of lactate, acetoacetate, etc. For example, some diabetic patients also develop lactic acidosis, in which blood lactate levels are greater than 5 mmol/liter. Thus, there remains a great need for glucose assays which are relatively insensitive to potentially interfering hydroxyl compounds, such as lactate.

BRIEF SUMMARY OF THE INVENTION

In one aspect, the present invention is directed to a method for detecting the presence or concentration of glucose in a sample which may also contain an α-hydroxy acid or a β-diketone, which comprises:

a) exposing the sample to a compound having at least two recognition elements for glucose, oriented such that the interaction between the compound and glucose is more stable than the interaction between the compound and the α-hydroxy acid or β-diketone, said compound also containing a detectable moiety having a detectable quality that changes in a concentration-dependent manner when said compound is exposed to glucose in said sample; and b) measuring any change in said detectable quality to thereby determine the presence or concentration of glucose in said sample, wherein the presence of the α-hydroxy acid or the β-diketone does not substantially interfere with said determination.

In another aspect, the present invention is directed to a compound having the following structure

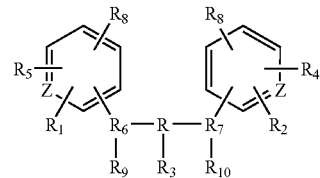

wherein:

$R_1$ and $R_2$ are the same or different and are selected from the following: i) hydrogen; ii) a substituent to modify the pKa and hydrolytic stability of the $R_8$ moiety, iii) a detectable moiety, or iv) a linking group capable of attachment to a solid support or a polymeric matrix, said support or matrix optionally containing a detectable moiety;

$R_3$ is hydrogen or a linking group capable of attachment to a solid support or a polymeric matrix, said support or matrix optionally containing a detectable moiety;

$R_4$ and $R_5$ are the same or different and are selected from the following: i) hydrogen, ii) a substituent to modify the pKa and hydrolytic stability of the $R_8$ moiety, iii) a detectable moiety, or iv) a linking group capable of attachment to a solid support or a polymeric matrix, said support or matrix optionally containing a detectable moiety;

each Z is independently carbon or nitrogen;

$R_6$ and $R_7$ are the same or different and are i) linking groups having from zero to ten contiguous or branched carbon and/or heteroatoms, or ii) a linking group capable of attachment to a solid support or a polymeric matrix, said support or matrix optionally containing a detectable moiety;

R is selected from the following: i) an aliphatic and/or aromatic spacer containing from 1 to 10 contiguous atoms selected from the group consisting of carbon, oxygen, nitrogen, sulfur and phosphorus, ii) a detectable moiety, or iii) a linking group capable of attachment to a solid support or a polymeric matrix, said support or matrix optionally containing a detectable moiety;

each $R_8$ is the same or different and is an optionally protected moiety which when unprotected is capable of interaction with the vicinal diol groups present in glucose; and $R_9$ and $R_{10}$ are the same or different, and are i) hydrogen, ii) a detectable moiety, iii) a group which is a) a linking group capable of attachment to a solid support or a polymeric matrix, said support or matrix optionally containing a detectable moiety, and/or b) includes a functional group capable of altering the physical properties of the compound;

with the proviso that the indicator compound contains at least one detectable moiety associated therewith, either directly or as part of the solid support or polymeric matrix.

In another aspect, the present invention is directed to a detection system which comprises a compound described above.

DETAILED DESCRIPTION OF THE INVENTION

Figure 1:
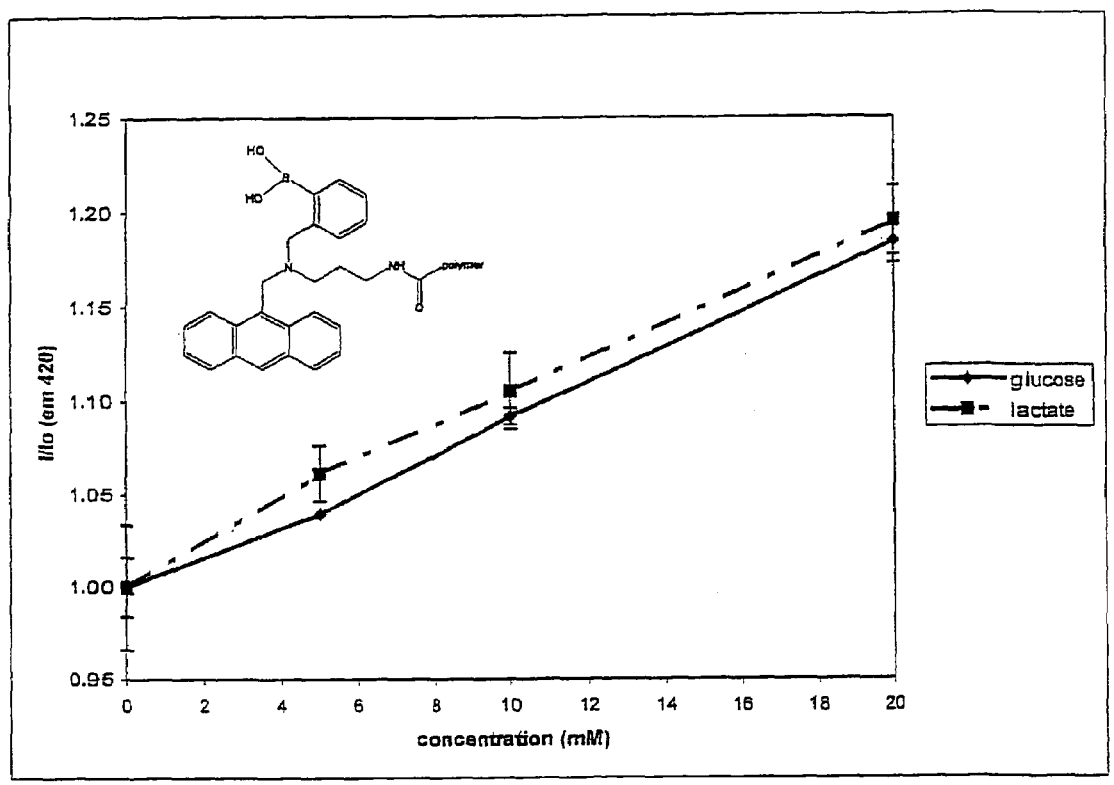
FIG. 1 illustrates the normalized fluorescence emission ($I/I_0$ @ 420 nm) of an indicator as described in Example 1.

In one aspect, the present invention provides a way to detect the presence or concentration of glucose in a sample which may also contain interfering compounds, such as α-hydroxy acids or β-diketones. Such potentially interfering compounds include lactate, acetoacetate, β-hydroxy butyric acid, etc.

The present invention is carried out using an indicator compound which is capable of recognizing glucose in a sample, but which is less likely to recognize interfering compounds in the sample. The indicator compound has at least two recognition elements for glucose, oriented such that the interaction between the indicator compound and glucose is more stable than the interaction between the indicator compound and the interfering compounds.

Suitable recognition elements include moieties which are capable of a preferably reversible interaction with glucose, especially with the diol groups present in glucose. Several such recognition elements are known, and preferably include boronic acid, boronate ion, arsenious acid, arsenite ion, telluric acid, tellurate ion, germanic acid, germanate ion, etc. Most preferred are recognition elements containing boron. It will be understood that until use, the recognition elements may be capped with a protecting group. Such groups are well known, and include neopentyl glycol, pinacol, etc. In certain embodiments, the capped recognition element is decapped in the medium in which the compound is to be used (see, e.g., Example 5).

The recognition elements are preferably spaced on the indicator compound a suitable distance from each other so as to allow at least two of the recognition elements to interact with a glucose molecule, resulting in increased specificity. In general, the recognition elements may have a spacer of up to about 30 atoms between them. Preferably, the recognition elements are oriented such that they are capable of being about 6 Å apart when interacting with glucose.

The indicator compounds of the present invention have a detectable quality that changes in a concentration-dependent manner when the compound is exposed to a sample containing glucose. Many such qualities are known and may be used in the present invention. For example, the indicator compound may include a luminescent (fluorescent or phosphorescent) or chemiluminescent moiety, an absorbance based moiety, etc. The indicator compound may include an energy donor moiety and an energy acceptor moiety, each spaced such that there is a detectable change when the indicator compound interacts with glucose. The indicator compound may include a fluorophore and a quencher, configured such that the fluorophore is quenched by the quencher when glucose is absent. In that situation, when glucose is present, the indicator undergoes a configurational change which causes the quencher to move sufficiently distant from the fluorophore so that fluorescence is emitted. Conversely, the fluorophore and quencher may be configured such that in the absence of glucose, they are sufficiently separated and the fluorophore emits fluorescence; upon interaction with glucose, the fluorophore and quencher are moved in sufficient proximity to cause quenching. The configurational change concept is described in more detail in our co-pending application Ser. No. 09/754,219, filed Jan. 5, 2001, entitled "Detection of Analytes", incorporated herein by reference.

Alternatively, the indicator may include a moiety such as a fluorophore capable of interacting with the recognition element or another moiety spatially disposed with respect to the recognition element such that in the absence of glucose, the fluorophore emits fluorescence. Upon addition of glucose, the glucose competes with the interaction between the fluorophore and the recognition element, or the interaction between the fluorophore and the other moiety spatially disposed with respect to the recognition element, causing a reduction in fluorescence. An example of that concept is illustrated in Example 6. It will also be recognized that the indicator may be chosen such that the fluorophore emits no fluorescence, or a relatively low level of fluorescence, when the fluorophore interacts with the recognition element or another moiety spatially disposed with respect to the recognition element in the absence of glucose. Upon addition of glucose, the glucose competes with the interaction between the fluorophore and the recognition element, or the interaction between the fluorophore and the other moiety spatially disposed with respect to the recognition element, causing an increase in fluorescence.

Other detectable moieties include those whose fluorescence is affected by glucose interaction via photoinduced electron transfer or inductive effects. These include the lanthanide chelates disclosed in copending U.S. application Ser. No. 09/265,979 filed Mar. 11, 1999 (and published as PCT International Application WO 99/46600 on Sep. 16, 1999), incorporated herein by reference; polyaromatic hydrocarbons and their derivatives; coumarins; BoDiPy; dansyl; catechols; etc. Another class of moieties include those whose absorbance spectrum changes upon interaction of the indicator compound with glucose, including Alizarin Red, etc. Another class of moieties include those whose fluorescence is modulated by proximity effects, e.g., energy donor/acceptor pairs such as dansyl/dabsyl, etc.

Preferably, the detectable quality is a detectable spectral change, such as changes in absorptive characteristics (e.g., absorbtivity and/or spectral shift), in fluorescent decay time (determined by time domain or frequency domain measurement), fluorescent intensity, fluorescent anisotropy or polarization; a spectral shift of the emission spectrum; a change in time-resolved anisotropy decay (determined by time domain or frequency domain measurement), etc.

The indicator compounds of the present invention, if soluble, may be used directly in solution if so desired. On the other hand, if the desired application so requires, the indicator compounds may be immobilized (such as by mechanical entrapment or covalent or ionic attachment) onto or within an insoluble surface or matrix such as glass, plastic, polymeric materials, etc. When the indicator compound is entrapped within, for example, another polymer, the entrapping material preferably should be sufficiently permeable to glucose to allow suitable interaction between glucose and the indicator compound.

If the indicator compounds are sparingly soluble or insoluble in water, yet detection in an aqueous medium is desired, the indicator compound may be co-polymerized with a hydrophilic monomer to form a hydrophilic macromolecule as described in co-pending U.S. application Ser. No. 09/632,624, filed Aug. 4, 2000, the contents of which are incorporated herein by reference.

Preferred indicator compounds have the following structure:

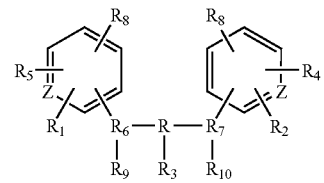

wherein:

$R_1$ and $R_2$ are the same or different and are selected from the following: i) hydrogen; ii) a substituent to modify the pKa and hydrolytic stability of the $R_8$ moiety, iii) a detectable moiety, or iv) a linking group capable of attachment to a solid support or a polymeric matrix, said support or matrix optionally containing a detectable moiety;

$R_3$ is hydrogen or a linking group capable of attachment to a solid support or a polymeric matrix, said support or matrix optionally containing a detectable moiety;

$R_4$ and $R_5$ are the same or different and are selected from the following: i) hydrogen, ii) a substituent to modify the pKa and hydrolytic stability of the $R_8$ moiety, iii) a detectable moiety, or iv) a linking group capable of attachment to a solid support or a polymeric matrix, said support or matrix optionally containing a detectable moiety;

each Z is independently carbon or nitrogen;

$R_6$ and $R_7$ are the same or different and are i) linking groups having from zero to ten contiguous or branched carbon and/or heteroatoms, or ii) a linking group capable of attachment to a solid support or a polymeric matrix, said support or matrix optionally containing a detectable moiety;

R is selected from the following: i) an aliphatic and/or aromatic spacer containing from 1 to 10 contiguous atoms selected from the group consisting of carbon, oxygen, nitrogen, sulfur and phosphorus, ii) a detectable moiety, or iii) a linking group capable of attachment to a solid support or a polymeric matrix, said support or matrix optionally containing a detectable moiety;

each $R_8$ is the same or different and is an optionally protected moiety which when unprotected is capable of interaction with the vicinal diol groups present in glucose; and $R_9$ and $R_{10}$ are the same or different, and are i) hydrogen, ii) a detectable moiety, iii) a group which is a) a linking group capable of attachment to a solid support or a polymeric matrix, said support or matrix optionally containing a detectable moiety, and/or b) includes a functional group capable of altering the physical properties of the compound;

with the proviso that the indicator compound contains at least one detectable moiety associated therewith, either directly or as part of the solid support or polymeric matrix.

Suitable groups for modifying the pKa and hydrolytic stability of the $R_8$ moieties would be readily apparent to one of ordinary skill, and include groups such as halogen; nitro; amino; halogen substituted alkyl; optionally substituted carboxyl; acyl; keto; nitrile; amide; ester; alkoxy; etc.

Suitable linking groups for any substituent may include groups from about 1 to about 20 contiguous atoms, which may be branched or substituted and which may include one or more heteroatoms, which terminate in a functional group capable of further reaction or attachment to a polymer or support. Examples of suitable linking groups include alkyl; aryl; acyl; polyamide; polyether; all optionally substituted, and combinations thereof.

$R_9$ and $R_{10}$ may further include functional groups capable of altering the physical properties of the compound, such as solubility, pKa, etc. For example, these include optionally substituted carboxylates, amino groups, quartenary ammonium groups, sulfonates, PEG, etc.

It will be understood that when any of the substituents is a detectable moiety, that could also include suitable linking groups which link the detectable moiety to the rest of the indicator compound. Suitable linking groups include those listed above. Suitable detectable moieties include those defined above.

$R_8$ is preferably selected from the group consisting of boronic acid, boronate ion, arsenious acid, arsenite ion, telluric acid, tellurate ion, germanic acid, germanate ion, and combinations thereof.

It will also be understood from the above definition that the present compounds and detection systems may be in polymeric form. Thus, an integral compound (containing recognition elements and detectable moiety) could be linked to an existing polymer, or the integral compound in monomeric form could be polymerized or co-polymerized with another suitable monomer to form a polymer. Alternatively, two separate monomeric components (e.g., one containing the recognition elements, and one containing a detectable moiety) could be co-polymerized so that the resulting polymer contains all necessary elements of the system (see Example 6).

Many uses exist for the indicator compounds of the present invention, including uses as indicators in the fields of energy, medicine and agriculture. For example, the indicator compounds can be used to detect sub-levels or supra-levels of glucose in physiological buffers or fluids, such as blood, plasma, serum, interstitial fluid, cerebrospinal fluid, urine, saliva, intraocular fluid, lymph, tears, or sweat, thus providing valuable information for diagnosing or monitoring such diseases as diabetes and adrenal insufficiency.

Medical/pharmaceutical production of glucose for human therapeutic application requires monitoring and control.

Uses for the present invention in agriculture include detecting levels of glucose in soybeans and other agricultural products. Glucose must be carefully monitored in critical harvest decisions for such high value products as wine grapes. As glucose is the most expensive carbon source and feedstock in fermentation processes, glucose monitoring for optimum reactor feed rate control is important in power alcohol production. Reactor mixing and control of glucose concentration also is critical to quality control during production of soft drinks and fermented beverages, which consumes the largest amounts of glucose and fermentable (vicinal diol) sugars internationally.

When the indicator compounds incorporate fluorescent indicator substituents, various detection techniques also are known in the art. For example, the compounds of the invention can be used in fluorescent sensing devices (e.g., U.S. Pat. No. 5,517,313) or can be bound to polymeric material such as test paper for visual inspection. This latter technique would permit, for example, glucose measurement in a manner analogous to determining pH with a strip of litmus paper. The compounds described herein may also be utilized as simple reagents with standard benchtop analytical instrumentation such as spectrofluorometers or clinical analyzers as made by Shimadzu, Hitachi, Jasco, Beckman and others. These molecules would also provide analyte specific chemical/optical signal transduction for fiber optic-based sensors and analytical fluorometers as made by Ocean Optics (Dunedin, Fla.), or Oriel Optics.

U.S. Pat. No. 5,517,313, the disclosure of which is incorporated herein by reference, describes a fluorescence sensing device in which the compounds of the present invention can be used to determine the presence or concentration of glucose in a liquid medium. The sensing device comprises a layered array of a fluorescent indicator molecule-containing matrix (hereafter "fluorescent matrix"), a high-pass filter and a photodetector. In this device, a light source, preferably a light-emitting diode ("LED"), is located at least partially within the indicator material, or in a waveguide upon which the indicator matrix is disposed, such that incident light from the light source causes the indicator molecules to fluoresce. The high-pass filter allows emitted light to reach the photodetector, while filtering out scattered incident light from the light source. The fluorescence of the indicator molecules employed in the device described in U.S. Pat. No. 5,517,313 is modulated, e.g., attenuated or enhanced, by the local presence of glucose.

In the sensor described in U.S. Pat. No. 5,517,313, the material which contains the indicator molecule is permeable to the analyte. Thus, the analyte can diffuse into the material from the surrounding test medium, thereby affecting the fluorescence emitted by the indicator compounds. The light source, indicator compound-containing material, high-pass filter and photodetector are configured such that at least a portion of the fluorescence emitted by the indicator compounds impacts the photodetector, generating an electrical signal which is indicative of the concentration of glucose in the surrounding medium.

In accordance with other possible embodiments for using the indicator compounds of the present invention, sensing devices also are described in U.S. Pat. Nos. 5,910,661, 5,917,605 and 5,894,351, all incorporated herein by reference.

The compounds of the present invention can also be used in an implantable device, for example to continuously monitor blood glucose levels in vivo. Suitable devices are described in, for example, co-pending U.S. patent application Ser. No. 09/383,148 filed Aug. 26, 1999, as well as U.S. Pat. Nos. 5,833,603, 6,002,954 and 6,011,984, all incorporated herein by reference.

The compounds of the present invention can be prepared by persons skilled in the art without an undue amount of experimentation using readily known reaction mechanisms and reagents, for example including reaction mechanisms which are consistent with the general procedures described below.

EXAMPLE 1

Water Soluble Copolymer of Anthracene Derivative and MAPTAC

I. Synthesis of Mono-Boronate-Anthracene Indicator Co-Polymerized in Water-Soluble Polymer A. 9-[3-(methacrylamido)propylamino]methylanthracene To a suspension of N-(3-aminopropyl)methacrylamide hydrochloride salt (11.82 g, 66.0 mmole, 3.0 equiv.) and DBMP (10 mg as inhibitor) in 250 mL $CHCl_3$ at 0° C. was added dropwise DIEA (18.5 g, 25.0 mL, 144 mmole, 6.5 equiv.) over a 20 min period. The mixture was allowed to warm to 25° C. and then recooled to 0° C. To the cooled mixture was added dropwise a solution of 9-chloromethylanthracene (5.0 g, 22 mmole) in $CHCl_3$ (100 mL) over a 1 hour period. The mixture was subsequently stirred at 25° C. for 1 hour, 50° C. for 12 hours and then 70° C. for 2 hours. At this time, the mixture was washed with 4×60 mL portions of water, and the combined aqueous layers were extracted with $CH_2Cl_2$. The combined organic extracts were dried over anhydrous $Na_2SO_4$, decanted and concentrated in vacuo. The crude material was purified by silica gel chromatography (flash silica gel, 2–5% $CH_3OH/CH_2Cl_2$) to yield 2.44 g (33%) of a solid product.

TLC: Merck silica gel 60 plates, Rf 0.39 with 90/10 $CH_2Cl_2/CH_3OH$, see with UV (254/366), ninhydrin stain.

B. 9-[N-[2-(5,5-dimethyl[1,3,2]dioxaborinan-2-yl)benzyl]-N-[3-(methacrylamido)propylamino]methylanthracene.

To a solution of 9-[3-(methacrylamido)propylamino]-methylanthracene (2.44 g, 7.34 mmole) and DBMP (10 mg as inhibitor) in 200 mL $CHCl_3$ at 0° C. was added DIEA (2.85 g, 3.84 mL, 22.0 mmole, 3.0 equiv.) in portions over a 10 min period, followed by the dropwise addition of a solution of (2-bromomethylphenyl)boronic acid neopentyl ester (2.49 g, 8.81 mmole, 1.2 equiv.) over a 30 min period. The mixture was subsequently stirred at 25° C. for 20 hours. At this time, the mixture was washed with water, and the combined aqueous layers were extracted with $CH_2Cl_2$. The combined organic extracts were dried over anhydrous $Na_2SO_4$, decanted and concentrated in vacuo. The crude material was purified by silica gel chromatography (flash silica gel, 2–5% $CH_3OH/CH_2Cl_2$) to yield 2.50 g (76%) of a lightly yellow crystalline solid.

Mp: 72–73° C.

TLC: Merck silica gel 60 plates, Rf 0.36 with 90/10 $CH_2Cl_2/CH_3OH$, see with UV (254/366), ninhydrin stain.

C. Water soluble copolymer of 9-[N-[2-(5,5-dimethyl-borinan-2-yl)benzyl]-N-[3-(methacrylamido)propylamino]-methylanthracene and MAPTAC (1:20 molar ratio).

To a solution of 9-[N-[2-(5,5-dimethyl[1,3,2]dioxaborinan-2-yl)-benzyl]-N-[3-(methacrylamido)propylamino]methylanthracene (0.0490 g, 0.105 mmole) and [3-(methacrylamido)propyl]-trimethylammonium chloride (MAPTAC, 50 wt % aqueous solution, 0.48 g, 0.90 mL, 2.1 mmole, 20 equiv.) in 1.5 mL ethylene glycol was added 4,4'-azobis (cyanovaleric acid) (0.008 g, 0.03 mmole, 1.4 mole % of total monomer). The solution was purged with argon gas for 5 minutes and then heated to 60° C. in the dark for 18 hours. At this time, the viscous solution was cooled to 25° C., diluted with 5 mL water and dialyzed through a cellulose acetate membrane (MWCO 3500) against 3×4 L of water. The dialyzed material was concentrated to dryness to yield 0.339 g (68%) of a yellow glassy solid.

II. Modulation of Fluorescence with Glucose and Lactate

The modulation of the fluorescence of the copolymer (which contains a single recognition element) prepared in this example by glucose and lactate was determined. FIG. 1 shows the normalized fluorescence emission (I/Io @ 420 nm) of 0.5 mg/mL solutions of the copolymer (1:20 molar ratio) in PBS containing a) 0–20 mM glucose; b) 0–20 mM lactate. Spectra were recorded using a Shimadzu RF-5301 spectrafluorometer with excitation @365 nm; excitation slits at 1.5 nm; emission slits at 5 nm; ambient temperature. Error bars are standard deviation with duplicate values for each data point. The fluorescence of the copolymer was affected by the presence of glucose and lactate.

EXAMPLE 2

Modulation of Bis-Boronate-Indicator Covalently Attached to Water-Soluble Polymer by Glucose and Potential Physiological Interferences I. Synthesis of Single-Methacrylate Monomer of Bis-Boronate-Anthracene Indicator

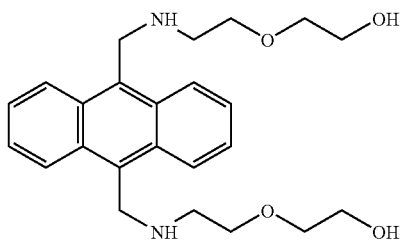

A. 9,10-bis[[2-(2-hydroxyethoxy)ethylamino]methyl]-anthracene.

To a solution of 2-(2-aminoethoxy)ethanol (31.4 g, 30.0 mL, 299 mmole, 20.9 equiv.) in 40 mL $CHCl_3$ at 23° C. was added 9,10-bis(chloromethyl)anthracene (3.94 g, 14.3 mmole). The solution was stirred in the dark for 67 hours. At this time, added 100 mL CH$_2$Cl$_2$ and washed with 1×50 mL and 2×100 mL portions of NaHCO$_3$ (saturated aqueous solution). The organic extract was dried over anhydrous Na$_2$SO$_4$, filtered and concentrated to yield 4.67 g (79%) of a yellow powder. Product (~85% pure by RP-HPLC) was carried on as is.

HPLC conditions: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 15.6 min.

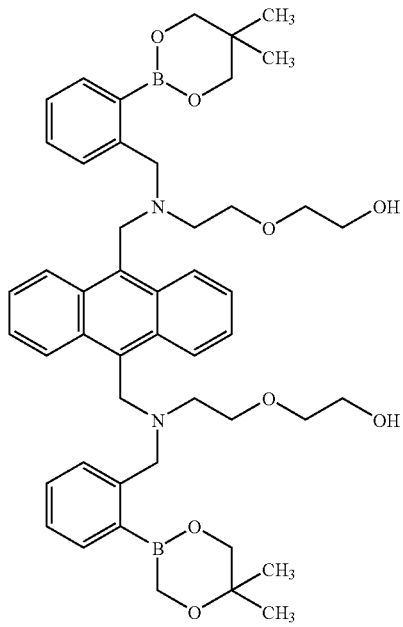

B. 9,10-bis[N-[2-(5,5-dimethyl[1,3,2]dioxaborinan-2-yl) benzyl]-N-[2-(2-hydroxyethoxy)ethylamino]methyl]anthracene.

A solution of 9,10-bis[[2-(2-hydroxyethoxy)-ethylamino] methyl]anthracene (4.02 g, 9.75 mmole), DIEA (12.6 g, 17.0 mL, 97.5 mmole, 10.0 equiv.) and (2-bromomethylphenyl) boronic acid neopentyl ester (13.7 g, 48 mmole, 4.9 equiv.) in 125 mL CHCl$_3$ at 23° C. was stirred in the dark for 46 hours. At this time, the reaction mixture was concentrated initially by rotary evaporation, then using a vacuum pump to remove the DIEA. The residue was purified by alumina column chromatography (150 g activated neutral alumina, 0–3% CH$_3$OH/CH$_2$Cl$_2$) to yield 5.67 g (70%) of a viscous oil which solidified upon standing. Product (~85% pure by RP-HPLC) was carried on as is.

TLC: Merck basic alumina plates, Rf 0.33 with 95/5 CH$_2$Cl$_2$/CH$_3$OH, see with UV (254/366).

HPLC conditions: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 18.8 min.

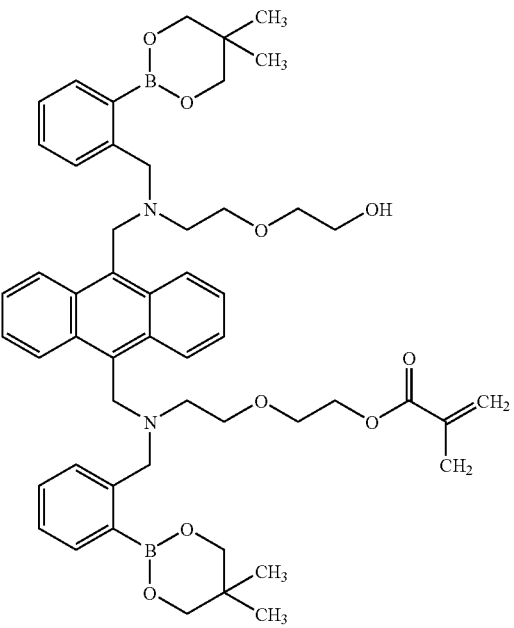

C. 9-[N-[2-(5,5-dimethyl[1,3,2]dioxaborinan-2-yl)benzyl]-N-[2-(2-methacroyloxyethoxy)ethylamino]methyl]-10-[N-[2-(5,5-dimethyl[1,3,2]dioxaborinan-2-yl)benzyl]-N-[2-(2-hydroxyethoxy)ethylamino]-methyl]anthracene. (Single-methacrylate monomer)

A solution of 9,10-bis[N-[2-(5,5-dimethyl-borinan-2-yl) benzyl]-N-[2-(2-hydroxyethoxy)ethylamino]-methyl]anthracene (0.298 g, 0.359 mmole), methacrylic acid (0.304 g, 0.300 mL, 3.53 mmole, 9.84 equiv.), DCC (0.965 g, 4.68 mmole, 13.0 equiv.) and N,N-dimethyl-aminopyridine (0.020 g, 0.16 mmole, 0.46 equiv.) in 15 mL CH$_2$Cl$_2$ at 23° C. was stirred in the dark for 4 hours. At this time, the reaction mixture was filtered and concentrated by rotary evaporation. The residue was purified by alumina column chromatography (50 g activated neutral alumina, 0–4% CH$_3$OH/CH$_2$Cl$_2$) to yield 0.150 g (47%) of a yellow solid.

FAB MS: Calc=d for C$_{52}$H$_{66}$B$_2$N$_2$O$_9$ [M]$^+$ 885. Found [M+1]$^+$ 886.

TLC: Merck basic alumina plates, Rf 0.45 with 95/5 CH$_2$Cl$_2$/CH$_3$OH, see with UV (254/366).

HPLC: HP 1100 HPLC chromatograph,Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 21 min.

D. Water soluble copolymer of 9-[N-[2-(5,5-dimethyl-borinan-2-yl)benzyl]-N-[2-(2-methacroyloxyethoxy)ethylamino]methyl-10-[N-[2-(5,5-dimethyl[1,3,2]dioxaborinan-2-yl)benzyl]-N-[2-(2-hydroxyethoxy)ethylamino]-methyl] anthracene and TMAMA (1:50 molar ratio).

To a solution of [2-(methacryloxy)ethyl]trimethyl-ammonium chloride (TMAMA, 70 wt % aqueous solution, 0.344 g monomer, 1.66 mmole, 50 equiv.) in 0.600 mL water was added a solution of 9-[N-[2-(5,5-dimethyl[1,3,2]dioxaborinan-2-yl)-benzyl]-N-[2-(2-methacroyloxyethoxy)ethylamino]methyl]-10-[N-[2-(5,5-dimethyl[1,3,2]dioxaborinan-2-yl)benzyl]-N-[2-(2-hydroxyethoxy)ethylamino]methyl]anthracene (0.0024 g, 0.0033 mmole) in 3.00 mL MeOH. To this mixture was added 4,4'-azobis(4-cyanovaleric acid) (0.0075 g, 0.027 mmole, 1.6 mole % of total monomer). The solution was filtered through a 0.45µ membrane filter, was purged with nitrogen gas and then heated in the dark at 55° C. for 16 hours. At this time, the viscous solution was cooled to 25° C. and concentrated in vacuo. The residue was diluted with 20 mL water and filtered through a 0.2µ membrane filter. The polymer solution was dialyzed through a cellulose acetate membrane (MWCO 3500) against 2×4 L of water. From the dialysis was obtained 38.5 mL of polymer solution. Concentration of a portion of this solution to dryness indicated 0.0075 g polymer per 1.0 mL solution. Overall 0.289 g (77%) yield of polymer.

II. Modulation of Fluorescence with Glucose, Lactate and Acetoacetate

Figure 2:
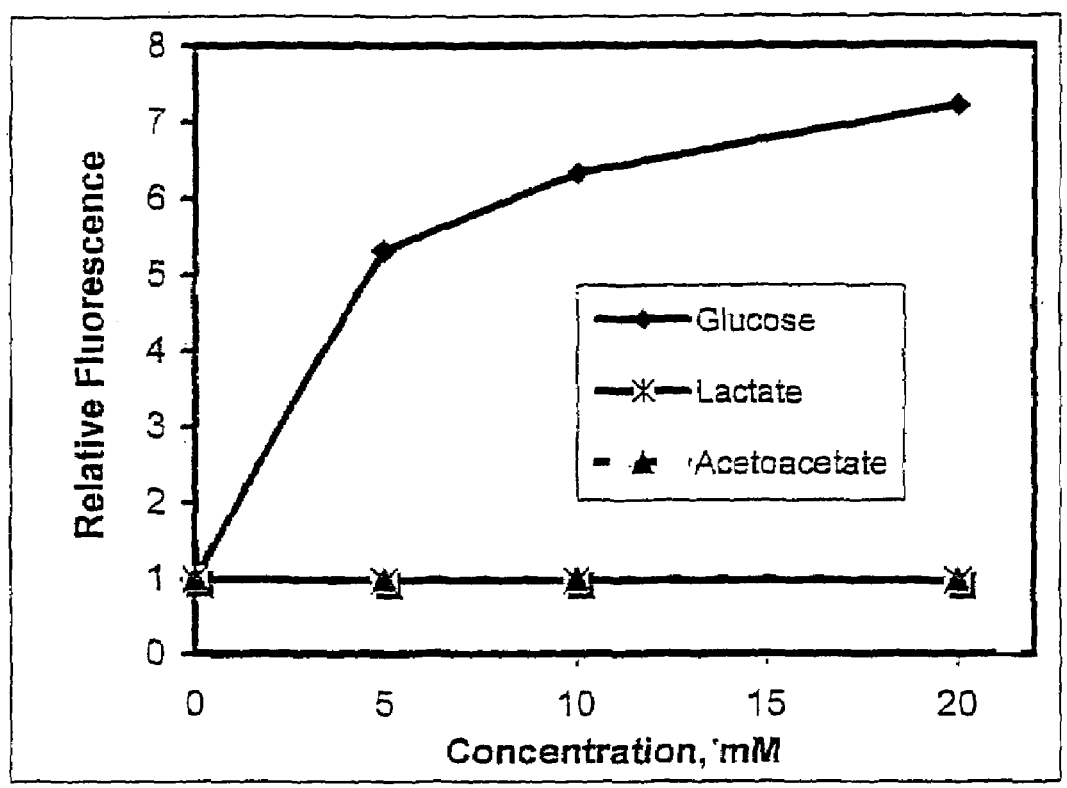
FIG. 2 illustrates the normalized fluorescence emission ($I/I_0$ @ 428 nm) of an indicator as described in Example 2.

The modulation of the fluorescence of the copolymer (which contains two recognition elements) prepared in this example by glucose, lactate and acetoacetate was determined. FIG. 2 shows the normalized fluorescence emission (I/Io @ 428 nm) of a 1.5 mg/mL solution of anthracene bis boronate-TMAMA (1:50 mole ratio) copolymer in PBS containing a) 0–20 mM glucose; b) 0–20 mM lactate; c) 0–20 mM lithium acetoacetate. Spectra were recorded using a Shimadzu RF-5301 spectrafluorometer with excitation @365 nm; excitation slits at 1.5 nm; emission slits at 1.5 nm; ambient temperature. The fluorescence of the copolymer was affected by the presence of glucose, but not by the presence of lactate or acetoacetate.

EXAMPLE 3

Effect of Lactate in Solution on the Dose Response Effect of Glucose on the Fluorescence of Bis-Boronate-Anthracene Indicator

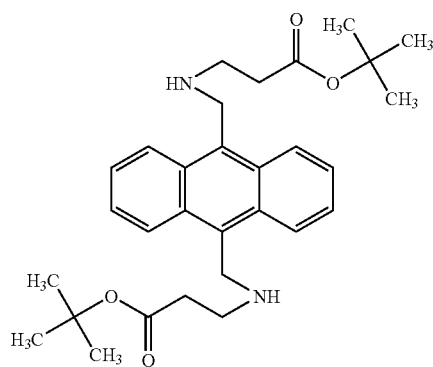

A. 9,10-bis[[2-(tert-butoxycarbonyl)ethylamino]methyl]-anthracene.

A solution of β-alanine tert-butyl ester hydrochloride (3.06 g, 16.8 mmole, 5.09 equiv.), DIEA (4.27 g, 5.75 mL, 33.0 mmole, 10.00 equiv.) and 9,10-bis(chloromethyl)anthracene (0.910 g, 3.31 mmole) in 75 mL CHCl$_3$ at 23° C. was stirred in the dark for 93 hours. At this time, the solution was filtered and washed with 1×40 mL and 2×60 mL portions of NaHCO$_3$ (saturated aqueous solution). The organic extract was dried over anhydrous Na$_2$SO$_4$, filtered and concentrated to yield a crude yellow solid. The residue was purified by silica gel column chromatography (30 g gravity grade gel, 0–3% CH$_3$OH/CH$_2$Cl$_2$) to yield 1.06 g (65%) of a viscous yellow-orange. Product was carried on as is.

TLC: Merck silica gel 60 plates, Rf 0.33 with 95/5 CH$_2$Cl$_2$/CH$_3$OH, see with UV (254/366).

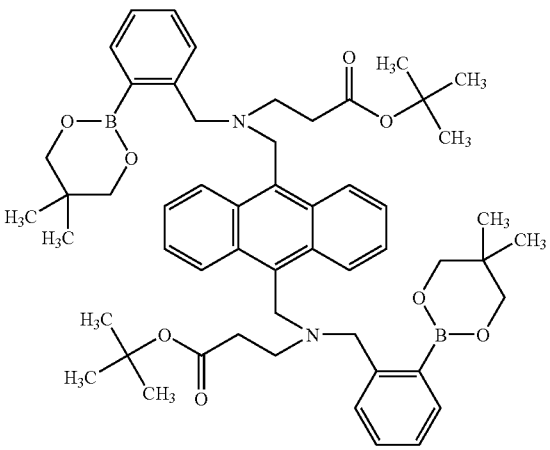

B. 9,10-bis[N-[2-(5,5-dimethyl[1,3,2]dioxaborinan-2-yl)benzyl]-N-[2-(tert-butoxycarbonyl)ethylamino]methyl]anthracene.

A solution of 9,10-bis[[2-(tert-butoxycarbonyl)-ethylamino]methyl]anthracene (1.60 g, 3.25 mmole), DIEA (4.45 g, 6.00 mL, 34.4 mmole, 10.6 equiv.) and (2-bromomethylphenyl)boronic acid neopentyl ester (4.80 g, 17.0 mmole, 5.22 equiv.) in 30 mL CHCl$_3$ at 23° C. was stirred in the dark for 4.5 days. At this time, 45 mL CHCl$_3$ were added to the mixture and the mixture was washed with 2×25 mL portions of NaHCO$_3$ (saturated aqueous solution). The organic extract was dried over anhydrous Na$_2$SO$_4$, filtered and concentrated to yield crude reddish oil. The residue was purified by alumina column chromatography (100 g activated neutral alumina, 0–3% CH$_3$OH/CH$_2$Cl$_2$) to yield ~3.5 g of an orange solid. The product was dissolved, followed by the formation of a white precipitate (DIEA-HBr salt). The solution was filtered and the filtrate concentrated to yield 2.72 g (93%) of an orange solid. Product (>80% pure by RP-HPLC) was carried on as is.

TLC: Merck basic alumina plates, Rf 0.66 with 95/5 CH$_2$Cl$_2$/CH$_3$OH, see with UV (254/366).

HPLC conditions: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 23.9 min.

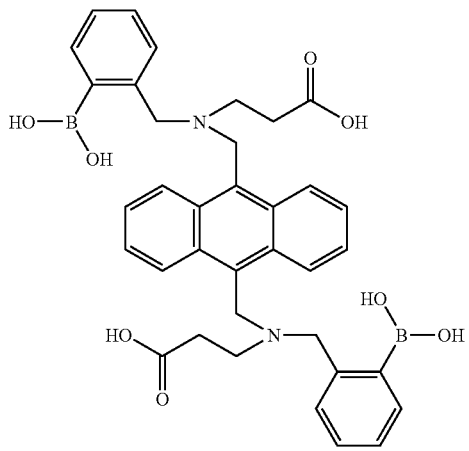

C. 9,10-bis[N-(2-boronobenzyl)-N-[2-(carboxyethyl)amino]-methyl]anthracene.

A solution of 9,10-bis[N-[2-(5,5-dimethyl[1,3,2]dioxaborinan-2-yl)benzyl]-N-[2-(tert-butoxycarbonyl)ethylamino]methyl]-anthracene (0.556 g, 0.620 mmole) in 5 mL 20% TFA/CH$_2$Cl$_2$ at 23° C. was stirred in the dark for 25 hours. At this time, the reaction mixture was concentrated under a stream of N$_2$ gas. The residue was triturated with 3×10 mL portions of ether. The residual solid was dried in vacuo to yield 0.351 g (87%) of a fluffy yellow powder.

FAB MS: Glycerol matrix; Calc=d for C$_{42}$H$_{46}$B$_2$N$_2$O$_{10}$ (bis glycerol adduct) [M]$^+$ 760. Found [M]$^+$ 760.

HPLC: HP 1100 HPLC chromatograph, Waters 5×100 mm NovaPak HR C18 column, 0.025 mL injection, 0.75 mL/min, 1.5 mL injection loop, 360 nm detection, A=water (0.1% HFBA) and B=MeCN (0.1% HFBA), gradient 10% B 2 min, 10–80% B over 18 min, 80–100% B over 2 min, 100% B 2 min, retention time 16.7 min.

D. Modulation of Fluorescence with Glucose and Lactate

Figure 3:
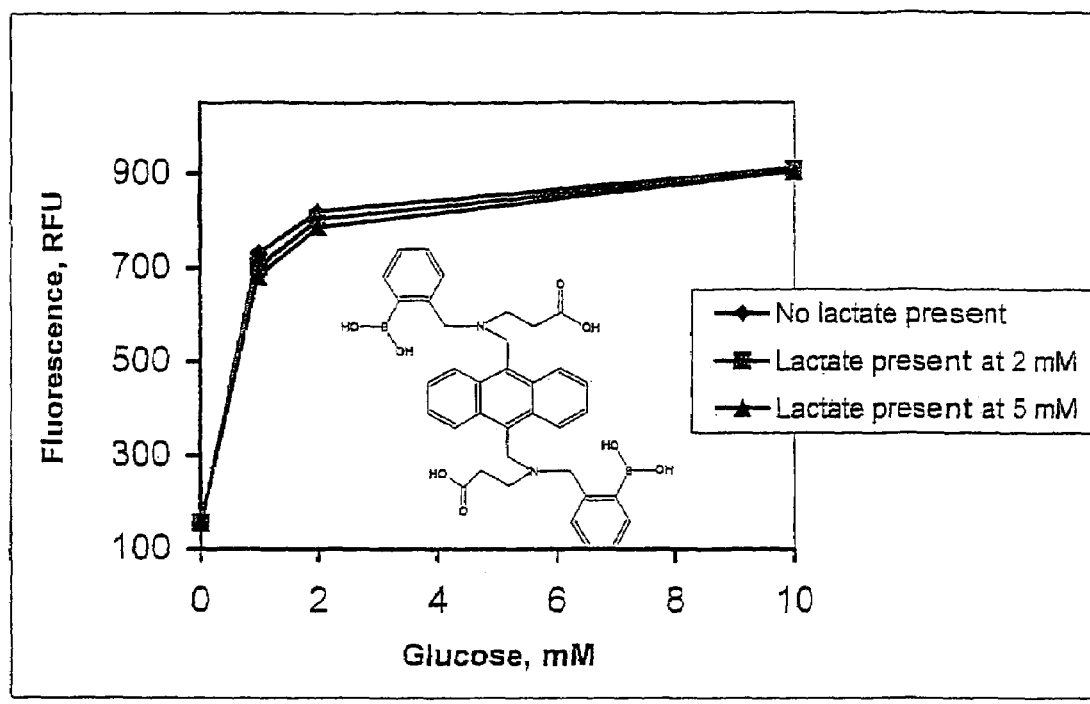
FIG. 3 illustrates the normalized fluorescence emission ($I/I_0$ @ 428 nm) of an indicator as described in Example 3.

The modulation of the fluorescence of the indicator compound (which contains two recognition elements) prepared in this example by glucose and lactate was determined. FIG. 3 shows the fluorescence (at 428 nm) of 75 µM solutions of bis carboxylate bis-boronate-anthracene indicator in PBS containing a) 0–10 mM glucose, 0 mM lactate; b) 0–10 mM glucose, 2 mM lactate; c) 0–10 mM glucose, 5 mM lactate. Spectra were recorded using a Shimadzu RF-5301 spectrafluorometer with excitation @365 nm; excitation slits at 1.5 nm; emission slits at 1.5 nm; ambient temperature. All points measured in triplicate, with ±1 SD error bars included. The presence of lactate did not substantially affect the fluorescence modulation of the indicator by glucose.

EXAMPLE 4

Selectivity of Bis-Boronate Glucose Indicator for Glucose vs. Lactate and Acetoacetate when Indicator Covalently Immobilized in the Hydrogel I. Preparation of Dual-Methacrylamide Monomer

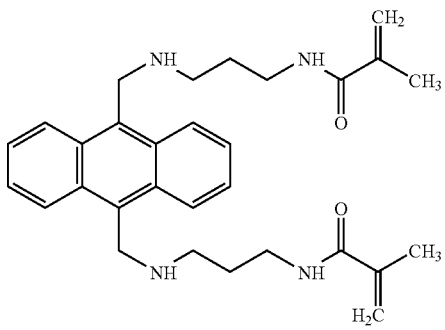

A. 9,10-bis[3-(methacrylamido)propylamino]-methylanthracene.

A suspension of 9,10-bis(chloromethyl)anthracene (1.5 g, 5.45 mmole), DIEA (28.17 g, 38.00 mL, 218 mmole, 40 equiv.), N-(3-aminopropyl)methacrylamide hydrochloride salt (9.76 g, 54.5 mmole, 10.0 equiv.), and ~5 mg of BHT in 200 mL CHCl$_3$ at 23° C. was stirred in the dark for 4 days at 40° C. At this time, the temperature was increased to 45° C. and the mixture was stirred for 3 days longer. At this time, a precipitate had formed. The mixture was filtered, and the solid product dissolved in the minimum amount of CH$_2$Cl$_2$. A yellow crystalline solid, the bis hydrochloride salt of the desired product, formed overnight (3.15 g, quantitative).

TLC: Merck basic alumina plates, Rf 0.31 with 90/10 CH$_2$Cl$_2$/CH$_3$OH, see with UV (254/366).

HPLC: HP 1100 HPLC chromatograph, Waters 5×100 mm NovaPak HR C18 column, 0.100 mL injection, 0.75 mL/min, 360 nm detection, A=water (0.1% HFBA) and B=MeCN (0.1% HFBA), gradient 10% B 2 min, 10–80% B over 18 min, 80–100% B over 2 min, 100% B 2 min, retention time 15.0 min.

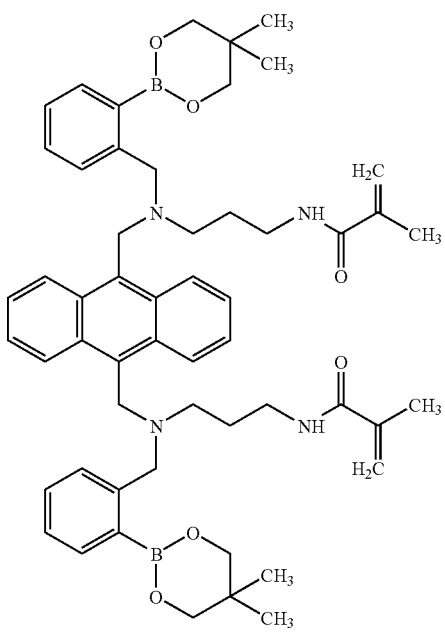

B. 9,10-bis[N-[2-(5,5-dimethyl[1,3,2]dioxaborinan-2-yl)benzyl]-N-[3-(methacrylamido)propylamino]methylanthracene. (Dual-Methacrylamide Monomer)

A solution of 9,10-bis[3-(methacrylamido)-propylamino]methylanthracene (0.0.650 g, 1.34 mmole of the free amine), DIEA (0.612 g, 0.825 mL, 4.74 mmole, 3.55 equiv.), (2-bromomethylphenyl)boronic acid neopentyl ester (1.34 g, 4.74 mmole, 3.55 equiv.) and BHT (5 mg as inhibitor) in 20 mL $CHCl_3$ at 23° C. was stirred in the dark for 5 days. At this time, the reaction mixture was concentrated in vacuo and the residue was purified by alumina chromatography (200 g activated neutral alumina, 0–2% $CH_3OH/CH_2Cl_2$) to yield 0.465 g (39%) of a very viscous yellow oil.

TLC: Merck basic alumina plates, Rf 0.59 with 90/10 $CH_2Cl_2/CH_3OH$, see with UV (254/366).

HPLC: HP 1100 HPLC chromatograph, Waters 5×100 mm NovaPak HR C18 column, 0.050 mL injection, 0.75 mL/min, 360 nm detection, A=water (0.1% HFBA) and B=MeCN (0.1% HFBA), gradient 10% B 2 min, 10–80% B over 18 min, 80–100% B over 2 min, 100% B 2 min, retention time 16.9 min.

C. Preparation of N,N-dimethylacrylamide Hydrogel with Glucose Indicator:

A solution of N,N-dimethylacrylamide (40% wt.) and N,N=-methylenebisacrylamide (0.8% wt.) in ethylene glycol was prepared. 9,10-bis[N-[2-(5,5-dimethyl[1,3,2]dioxaborinan-2-yl)-benzyl]-N-[3-(methacrylamido)propylamino]methylanthracene (17.8 mg, $2 \times 10^{-5}$ mole) and 40 μL of aqueous ammonium persulfate (5% wt) were combined with 1 mL of ethylene glycol monomer solution. The resulting solution was placed in a glove box purged with nitrogen. An aqueous solution of N,N,N=,N=-tetramethylethylenediamine (80 μL, 5% wt.) was added to the monomer formulation to accelerate polymerization. The resulting formulation was poured in a mold constructed from microscope slides and 100 micron stainless steel spacer. After being kept for 8 hours in nitrogen atmosphere the mold was placed in phosphate buffered saline (PBS) (10 mM PBS, pH=7.4), the microscope slides were separated, and the hydrogel was removed. The hydrogel was washed with 100 mL of PBS containing 1 mM lauryl sulfate sodium salt and 1 mM EDTA sodium salt for 3 days, the solution being changed every day, followed by washing with DMF/PBS (10/90 by vol., 3×100 mL), and finally with PBS (pH=7.4, 3×100 mL). The resulting hydrogel polymer was stored in PBS (10 mM PBS, pH=7.4) containing 0.2% wt. sodium azide and 1 mM EDTA sodium salt.

II. Modulation of Fluorescence with Glucose, Lactate and Acetoacetate

Figure 4:
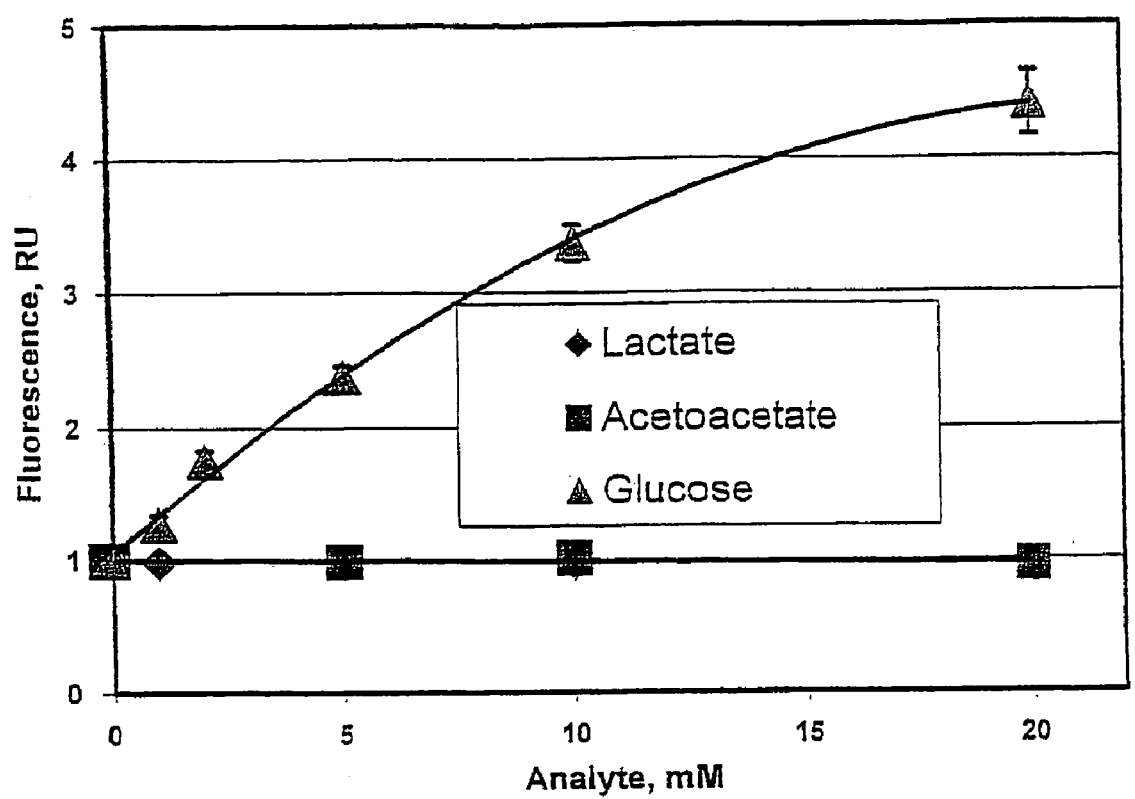
FIG. 4 illustrates the normalized fluorescence emission ($I/I_0$ @ 427 nm) of an indicator as described in Example 4.

The modulation of the fluorescence of the indicator compound (which contains two recognition elements) prepared in this example by glucose, lactate and acetoacetate was determined. FIG. 4 shows the normalized fluorescence emission (I/Io @ 427 nm) of a hydrogel containing the glucose recognition molecule of this example in 10 mM PBS, pH 7.4 containing 0.2% $NaN_3$ and 1 mM EDTA containing various amounts of sodium-L-lactate, lithium acetoacetate or α-D-glucose. Data were recorded using a Shimadzu RF-5301 spectrofluorometer with excitation @365 nm (slit=3 nm) and emission at 427 nm (slit=3 nm) at low sensitivity at 37° C. using a temperature controlled sample holder. The cuvettes containing 3 mL of the desired solution were equilibrated at 37° C. for 15 minutes before measurement. Each hydrogel sample was measured in four independent samples. Error bars are standard deviation with quadruplicate values for each data point. The hydrogels containing a glucose recognition molecule were prepared as previously described. The hydrogels were mounted on glass slides and covered with polyester mesh in PMMA cuvettes at 45□ to the incident light. Solutions of 1, 5, 10 and 20 mM sodium L-lactate [Aldrich], 5, 10 and 20 mM lithium acetoacetate [Aldrich], and 1, 2, 4, 5, 10, and 20 mM α-D-glucose were prepared in 10 mM PBS, pH 7.4 containing 0.2% $NaN_3$ and 1 mM EDTA. The fluorescence of the copolymer was affected by the presence of glucose, but not by the presence of lactate or acetoacetate.

EXAMPLE 5

Glucose Selectivity vs. Lactate Using Bis-Boronate Recognition and Proximity Quenching Signal Generation A. N-(2,2-diethoxyethyl)-4-bromo-1,8-naphthalimide.

A suspension of 4-bromo-1,8-naphthalic anhydride (10.0 g, 36.1 mmol) and aminoacetaldehyde diethyl acetal (4.81 g, 5.26 mL, 36.1 mmol, 1 equiv.) in 45 mL EtOH was stirred at 45° C. for 3 days. At this time, the resulting suspension was filtered, washing with EtOH and the residue was dried to yield 13.3 g (94%) of a light brown solid product.

TLC: Merck silica gel 60 plates plates, Rf 0.17 with 98/2 $CH_2Cl_2/CH_3OH$, see with UV (254/366).

HPLC: HP 1100 HPLC chromatograph, Waters 5×100 mm NovaPak HR C18 column, 0.050 mL injection, 0.75 mL/min, 1.5 mL injection loop, 360 nm detection, A=water (0.1% HFBA) and B=MeCN (0.1% HFBA), gradient 10% B 2 min, 10–80% B over 18 min, 80–100% B over 2 min, 100% B 2 min, retention time 24.2 min.

B. N-(2,2-diethoxyethyl)-4-butylamino-1,8-naphthalimide.

A solution of N-(2,2-diethoxyethyl)-4-bromo-1,8-naphthalimide (0.797 g, 2.03 mmol) and n-butylamine (1.48 g, 2.00 mL, 20.2 mmol, 9.96 equiv.) in 8 mL NMP was heated at 45° C. for 66 hours. At this time, the resulting suspension was allowed to cool to 25° C., followed by filtration. The residue was dissolved with 50 mL ether and extracted 3×50 mL water. The organic extract was dried over anhydrous $Na_2SO_4$, filtered and concentrated to yield a crude yellow powder. The crude material was purified by silica gel chromatography (25 g gravity grade gel, 0–1% $CH_3OH/CH_2Cl_2$) to yield 0.639 g (82%) of a yellow powder.

TLC: Merck silica gel 60 plates, Rf 0.71 with 95/5 $CH_2Cl_2/CH_3OH$, see with UV (254/366).

HPLC: HP 1100 HPLC chromatograph, Waters 5×100 mm NovaPak HR C18 column, 0.050 mL injection, 0.75 mL/min, 1.5 mL injection loop, 450 nm detection, A=water (0.1% HFBA) and B=MeCN (0.1% HFBA), gradient 10% B 2 min, 10–80% B over 18 min, 80–100% B over 2 min, 100% B 2 min, retention time 23.5 min.

C. N-(2-oxoethyl)-4-butylamino-1,8-naphthalimide.

A solution of N-(2,2-diethoxyethyl)-4-butylamino-1,8-naphthalimide (0.622 g, 1.62 mmol) and p-toluene-sulfonic acid mono hydrate (0.010 g, 0.053 mmol, 0.032 equiv.) in 25 mL acetone was stirred at 25° C. for 18 hours. At this time, the solution was concentrated and the residue purified by silica gel chromatography (25 g gravity grade gel, 0–1% $CH_3OH/CH_2Cl_2$) to yield 0.470 g (94%) of an orange solid.

TLC: Merck silica gel 60 plates, Rf 0.61 with 95/5 $CH_2Cl_2/CH_3OH$, see with UV (254/366).

$^1$H NMR (400 MHZ, $CDCl_3$); δ 1.03 (t, 3H, J=7.3 Hz), 1.53 (m, 2H), 1.78 (m, 2H), 3.38 (t, 2H, J=7.2 Hz), 5.02 (s, 2H), 6.64 (d, 1H, J=8.6 Hz), 7.52 (dd, 1H, J=7.4, 8.3 Hz), 8.08 (dd, 1H, J=1 Hz, 8.5 Hz), 8.38 (d, 1H, J=8.3 Hz), 8.46 (dd, 1 H, J=1.0, 7.3 Hz), 9.75 (s, 1H).

HPLC: HP 1100 HPLC chromatograph, Waters 5×100 mm NovaPak HR C18 column, 0.050 mL injection, 0.75 mL/min, 1.5 mL injection loop, 450 nm detection, A=water (0.1% HFBA) and B=MeCN (0.1% HFBA), gradient 10% B 2 min, 10–80% B over 18 min, 80–100% B over 2 min, 100% B 2 min, retention time 19.6 min.

D. N-(4-dimethylaminobenzyl)-1,6-diaminohexane.

A suspension of 4-dimethylaminobenzaldehyde (1.00 g, 6.70 mmol), $Na_2SO_4$ (6.70 g, 47.2 mmol, 7.04 equiv.) and 1,6-diaminohexane (3.89 g, 33.5 mmol, 5.00 equiv.) in 20 mL anhydrous EtOH was stirred in the dark at 25° C. under an atmosphere of nitrogen gas for 18 hours. At this time, the solution was filtered and $NaBH_4$ (1.73 g, 45.8 mmol, 6.84 equiv.) was added to the filtrate. The suspension was stirred at 25° C. for 5 hours. At this time, the reaction mixture was concentrated and the residue dissolved in 50 mL water and extracted 3×50 mL ether. The combined organic extracts were washed 2×50 mL water. The combined aqueous extracts were extracted 2×50 mL ether. The combined organic extracts were dried over $Na_2SO_4$, filtered and concentrated to yield 1.35 g (81%) of a viscous oil.

TLC: Merck silica gel 60 plates plates, Rf 0.58 with 80/15/5 $CH_2Cl_2/CH_3OH/iPrNH_2$, see with ninhydrin stain, UV (254/366).

HPLC: HP 1100 HPLC chromatograph, Waters 5×100 mm NovaPak HR C18 column, 0.050 mL injection, 0.75 mL/min, 1.5 mL injection loop, 280 nm detection, A=water (0.1% HFBA) and B=MeCN (0.1% HFBA), gradient 10% B 2 min, 10–80% B over 18 min, 80–100% B over 2 min, 100% B 2 min, retention time 13.3 min.

E. N-2-[6-N(N-4-dimethylaminobenzyl)aminohexyl]aminoethyl)-4-butylamino-1,8-naphthalimide.

To a suspension of N-(2-oxoethyl)-4-butylamino-1,8-naphthalimide (0.346 g, 1.11 mmol) in 25 mL anhydrous MeOH was added a solution of N-(4-dimethylaminobenzyl)-1,6-diaminohexane (0.554 g, 2.22 mmol, 2.00 equiv.) and acetic acid (0.067 g, 1.1 mmol, 1.0 equiv.) in 20 mL anhydrous MeOH. To this mixture was added a solution of $NaCNBH_3$ (0.070 g, 1.1 mmol, 1.0 equiv.) in 5 mL anhydrous MeOH. The reaction mixture was stirred at 25° C. for 15 hours. At this time, the MeOH was removed by rotary evaporation and the residue was dissolved in 30 mL water. The solution was adjusted to pH 2 with 1 N HCl and then stirred for 1 hour at 25° C. At this time, the solution was adjusted to pH 12 with 1 N NaOH and subsequently extracted 3×50 mL $CH_2Cl_2$. The combined organic extracts were washed 3×50 mL water, dried over anhydrous $Na_2SO_4$, filtered and concentrated to yield a crude brown oil. The crude material was purified by silica gel chromatography (35 g flash grade gel, 0–50% $CH_3OH/CH_2Cl_2$, then 45/50/5 $CH_3OH/CH_2Cl_2/iPrNH_2$) to yield 0.190 g (32%) of diamine product.

FAB MS: Calc=d for $C_{33}H_{45}N_5O_2$ $[M]^+$ 544. Found $[M]^+$ 544.

TLC: Merck silica gel 60 plates, Rf 0.42 with 80/20 $CH_2Cl_2/CH_3OH$, see with ninhydrin stain and UV (254/366).

HPLC: HP 1100 HPLC chromatograph, Waters 5×100 mm NovaPak HR C18 column, 0.050 mL injection, 0.75 mL/min, 1.5 mL injection loop, 450 nm detection, A=water (0.1% HFBA) and B=MeCN (0.1% HFBA), gradient 10% B 2 min, 10–80% B over 18 min, 80–100% B over 2 min, 100% B 2 min, retention time 17.6 min.

F. N-2-[6-N-(N-4-dimethylaminobenzyl)-6-N-[2-(5,5-dimethylborinan-2-yl)benzyl]aminohexyl]-[2-(5,5-dimethylborinan-2-yl)benzyl]aminoethyl-4-butylamino-1,8-naphthalimide.

To a solution of N-2-[6-N-(N-4-dimethylaminobenzyl)-aminohexyl]aminoethyl)-4-butylamino-1,8-naphthalimide (0.150 g, 0.276 mmole) and DIEA (0.355 g, 0.478 mL, 2.81 mmole, 10.0 equiv.) in 5 mL $CHCl_3$ was added a solution of (2-bromomethylphenyl)boronic acid neopentyl ester (0.390 g, 1.38 mmole, 5.00 equiv.) in 2 mL $CHCl_3$. The solution was subsequently stirred at 25° C. for 27 hours. At this time, the mixture was concentrated and the residue was purified by alumina column chromatography (100 g activated neutral alumina, 0–5% $CH_3OH/CH_2Cl_2$) to yield 0.024 g (19%) of a viscous brown oil.

FAB MS (glycerol matrix): Calc'd for $C_{53}H_{67}B_2N_5O_8$ $[M]^+$ 924 (bis glycerol adduct in place of bis neopentyl ester of boronic acids). Found $[M]^+$ 924.

TLC: Merck neutral alumina plates, Rf 0.62 with 80/20 $CH_2Cl_2/CH_3OH$, see with UV (254/366).

HPLC: HP 1100 HPLC chromatograph, Waters 5×100 mm NovaPak HR C18 column, 0.050 mL injection, 0.75 mL/min, 1.5 mL injection loop, 450 nm detection, A=water (0.1% HFBA) and B=MeCN (0.1% HFBA), gradient 10% B 2 min, 10–80% B over 18 min, 80–100% B over 2 min, 100% B 2 min, retention time 20.7 min.

G. N-2-[6-N-(N-4-dimethylaminobenzyl)-6-N-[2-(borono)benzyl]aminohexyl]-[2-(borono)benzyl]amino-ethyl-4-butylamino-1,8-naphthalimide (nBuF-hexa-Q bis-boronate).

The free bis boronic acid product used in glucose studies results from dissolution of N-2-[6-N-(N-4-dimethyl-aminobenzyl)-6-N-[2-(5,5-dimethyl[1,3,2]dioxaborinan-2-yl) benzyl]amino-hexyl]-[2-(5,5-dimethyl[1,3,2]dioxaborinan-2-yl)benzyl]aminoethyl-4-butylamino-1,8-naphthalimide in the MeOH/PBS buffer system.

H. Modulation of Fluorescence with Glucose and Lactate.

Figure 5:
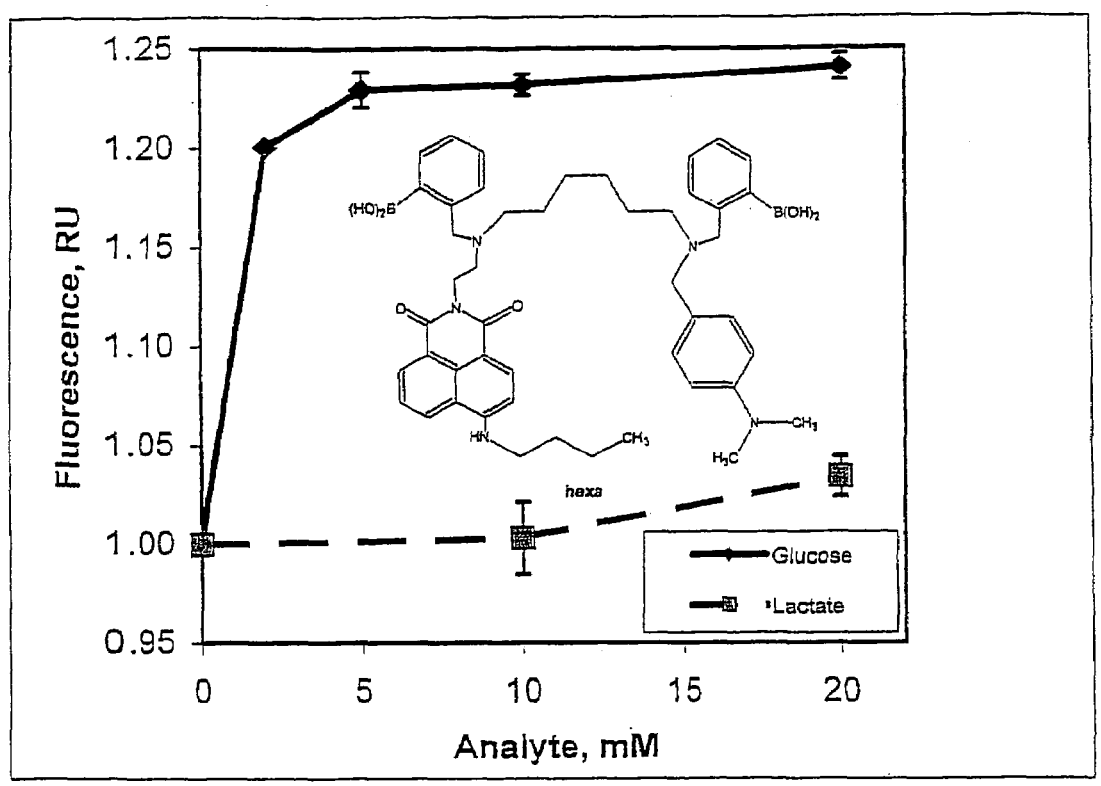
FIG. 5 illustrates the normalized fluorescence emission ($I/I_0$ @ 540 nm) of an indicator as described in Example 5.

The modulation of the fluorescence of the indicator compound (which contains two recognition elements) prepared in this sample by glucose and lactate was determined. FIG. 5 shows the normalized fluorescence emission (I/Io @ 535 nm) of 0.015 mM solutions of the indicator compund in 70/30 MeOH/PBS containing a) 0–20 mM glucose; b) 0–20 mM lactate. Spectra were recorded using a Shimadzu RF-5301 spectrafluorometer with excitation @ 450 nm; excitation slits at 1.5 nm; emission slits at 1.5 nm; ambient temperature. Error bars are standard deviation with triplicate values for each data point. The fluorescence of the indicator was affected by the presence of glucose, but not substantially affected by the presence of lactate.

EXAMPLE 6

Effect of Glucose or Lactate on Acrylamide Gel Containing N-[3-(methacrylamido)propyl]-3,4-dihydroxy-9,10-dioxo-2-anthracenesulfonamide (Alizarin Red S Monomer) and α,α'-bis[N-[2-(5,5-dimethyl[1,3,2]dioxaborinan-2-yl)benzyl]-N-[3-(methacrylamido)propylamino]-1,4-xylene (bis Boronic Acid Monomer)

A. 3,4-Dihydroxy-9,10-dioxo-2-anthracenesulfonyl chloride:

3,4-dihydroxy-9,10-dioxo-2-anthracenesulfonic acid sodium salt (1.4 g, 3.9 mmoles) was combined with 30 mL of chlorosulfonic acid and heated to 90° C. for 5 hours, after which the solution was cooled to 0° C. and poured into 100 g of ice. After the ice melted the solution was extracted with $CH_2Cl_2$ (3×100 mL), methylene chloride extracts were combined, dried with $Na_2SO_4$ and evaporated to produce 0.87 g of solid (Yield 66%).

B. N-[3-(methacrylamido)propyl]-3,4-dihydroxy-9,10-dioxo-2-anthracenesulfonamide:

3,4-dihydroxy-9,10-dioxo-2-anthracenesulfonyl chloride (96 mg, 0.28 mmoles) and N-(3-aminopropyl) methacrylamide hydrochloride (108 mg, 0.6 mmoles) were combined with 20 mL of $CH_2Cl_2$. To this suspension $Et_3N$ (303 mg, 3 mmoles) was added. The mixture was stirred at room temperature for 24 hours, filtered, and solvent was evaporated. The resulting solid was subjected to column chomatography on $SiO_2$ (10 g) with $CH_2Cl_2$/MeOH (90/10) as an eluent. The product was obtained as a red solid (80 mg, 64% yield).

FAB MS: Calculated for $C_{21}H_{20}N_2O_7S$ $M^+$ 445. Found $M^+$ 445.

HPLC: HP 1100 HPLC chromatograph, Waters 5×100 mm NovaPak HR C18 column, 0.100 mL injection, 0.75 mL/min, 2 mL injection loop, 370 nm detection, A=water (0.1% HFBA) and B=MeCN (0.1% HFBA), gradient 10% B 2 min, 10–80% B over 18 min, 80–100% B over 2 min, 100% B 2 min, retention time 17.67 min.

C. α,α'-bis[3-(methacrylamido)propylamino]-1,4-xylene.

A solution of N-(3-aminopropyl)methacrylamide hydrochloride salt (3.00 g, 16.8 mmole, 2.21 equiv.), DIEA (6.5 g, 8.8 mL, 50 mmole, 6.6 equiv.), terephthaldicarboxaldehyde (1.02 g, 7.60 mmole) and $Na_2SO_4$ (10.7 g, 75.3 mmole, 9.91 equiv.) in 75 mL anhydrous MeOH was stirred in the dark at 25° C. for 18 hours. At this time, more $Na_2SO_4$ (10.7 g, 75.3 mmole, 9.91 equiv.) was added and stirring continued for 6 hours longer. At this time, the solution was filtered and $NaBH_4$ (1.73 g, 45.7 mmole, 6.01 equiv.) was added to the filtrate in portions and subsequently stirred at 25° C. for 21 hours. The suspension was filtered through Celite and the filtrate was concentrated. The residue was dissolved in 100 mL $CH_2Cl_2$ and washed 1×25 mL saturated aqueous $NaHCO_3$. The organic extract was dried over anhydrous $Na_2SO_4$, filtered and concentrated to yield a viscous oil. The product was carried on as is.

HPLC: HP 1100 HPLC chromatograph, Vydac 201TP 10×250 mm column, 0.100 mL injection, 2.00 mL/min, 260 nm detection, A=water (0.1% HFBA) and B=MeCN (0.1% HFBA), gradient 10% B 2 min, 10–80% B over 18 min, 80–100% B over 2 min, 100% B 2 min, retention time 15.8 min.

D. α,α=-bis[N-[2-(5,5-dimethyl[1,3,2]dioxaborinan-2-yl)benzyl]-N-[3-(methacrylamido)propylamino]-1,4-xylene.

A solution of α,α=-bis[3-(methacrylamido)-propylamino]-1,4-xylene (2.94 g, 7.61 mmole), DIEA (2.97 g, 4.00 mL, 23.0 mmoles, 3.02 equiv.), (2-bromomethylphenyl)boronic acid neopentyl ester (6.50 g, 23.0 mmole, 3.02 equiv.) and BHT (5 mg as inhibitor) in 75 mL $CH_2Cl_2$ at 25° C. was stirred in the dark for 28 hours. At this time, the mixture was washed 1×25 mL saturated aqueous $NaHCO_3$. The organic extract was dried over anhydrous $Na_2SO_4$, filtered and concentrated. To the residue was added 200 mL ether and the suspension was stirred for 18 hours. The suspension was filtered and the residue dissolved in $CH_2Cl_2$, filtered and the filtrate concentrated. To the solid residue was added 150 mL ether and the suspension was stirred for 18 hours. At this time, the suspension was filtered yielding 1.98 g (33%) of a fluffy pink powder.

FAB MS: Calc=d for $C_{46}H_{64}B_2N_4O_6$ $[M]^+$ 790. Found $[M+1]^+$ 791.

HPLC: HP 1100 HPLC chromatograph, Waters 5×100 mm NovaPak HR C18 column, 0.050 mL injection, 0.75 mL/min, 280 nm detection, A=water (0.1% HFBA) and B=MeCN (0.1% HFBA), gradient 10% B 2 min. 10–80% B over 18 min, 80–100% B over 2 min, 100% B 2 min, retention time 13.4 min.

E. Preparation of Acrylamide Gel Containing N-[3-(methacrylamido)propyl]-3,4-dihydroxy-9,10-dioxo-2-anthracenesulfonamide (Alizarin Red S Monomer) and α,α'-bis[N-[2-(5,5-dimethyl[1,3,2]dioxaborinan-2-yl)benzyl]-N-[3-(methacrylamido)propylamino]-1,4-xylene:

Ethylene glycol solution containing 30% wt. acrylamide and 0.8% wt. N,N'-methylenebisacrylamide was prepared.

N-[3-(methacrylamido)propyl]-3,4-dihydroxy-9,10-dioxo-2-a nthracenesulfonamide (1.5 mg, $3.38 \times 10^{-6}$ mole) and α,α'-bis[N-[2-(5,5-dimethylborinan-2-yl)benzyl]-N-[3-(methacrylamido)propylamino]-1, 4-xylene (28 mg, $3.54 \times 10^{-5}$ mole) were combined with 800 μL of ethylene glycol monomer solution and 40 μL of 5% wt. aqueous ammonium persulfate. This formulation was placed in a glove box purged with nitrogen along with a mold constructed from glass microscope slides and 100 micron stainless steel spacer. An aqueous solution of N,N,N',N'-tetramethylethylenediamine (40 μL, 5% wt.) was added to the monomer solution to accelerate polymerization and the final formulation was poured into a glass mold. The mold was left under nitrogen atmosphere for 16 hours, after which it was immersed in PBS (pH=7.4) and the glass slides were separated to afford a hydrogel polymer in a form of a thin film. The resulting hydrogel thin film was washed with 100 mL of phosphate buffered saline containing 1 mM lauryl sulfate sodium salt for 3 days, the solution being changed every day, followed by washing with MeOH/PBS (20/80 by vol., 3×100 mL), and finally with PBS (pH=7.4, 3×100 mL). Hydrogel polymer was stored in PBS (10 mM PBS, pH=7.4) containing 0.2% wt. sodium azide and 1 mM EDTA sodium salt.

F. Modulation of Absorbance With Glucose and Lactate

The modulation of the absorbance of the indicator hydrogel (which contains two recognition elements) prepared in this example by glucose and lactate was determined. The acrylamide gel was mounted in PMMA cell in the same way as described in Example 4. Phosphate buffered saline (PBS), pH=7.4 containing desired amount of glucose or sodium lactate was heated to 37° C. in a water bath and placed in the PMMA cell containing the gel after which the PMMA cell was allowed to equilibrate for 15 min at 37° C. Absorbance measurement for each glucose or lactate concentration was conducted in triplicate. For each measurement, absorbance at 650 nm was used as a blank, A(650 nm) was subtracted from all values of A(450 nm) and A(530 nm).

Figure 6:
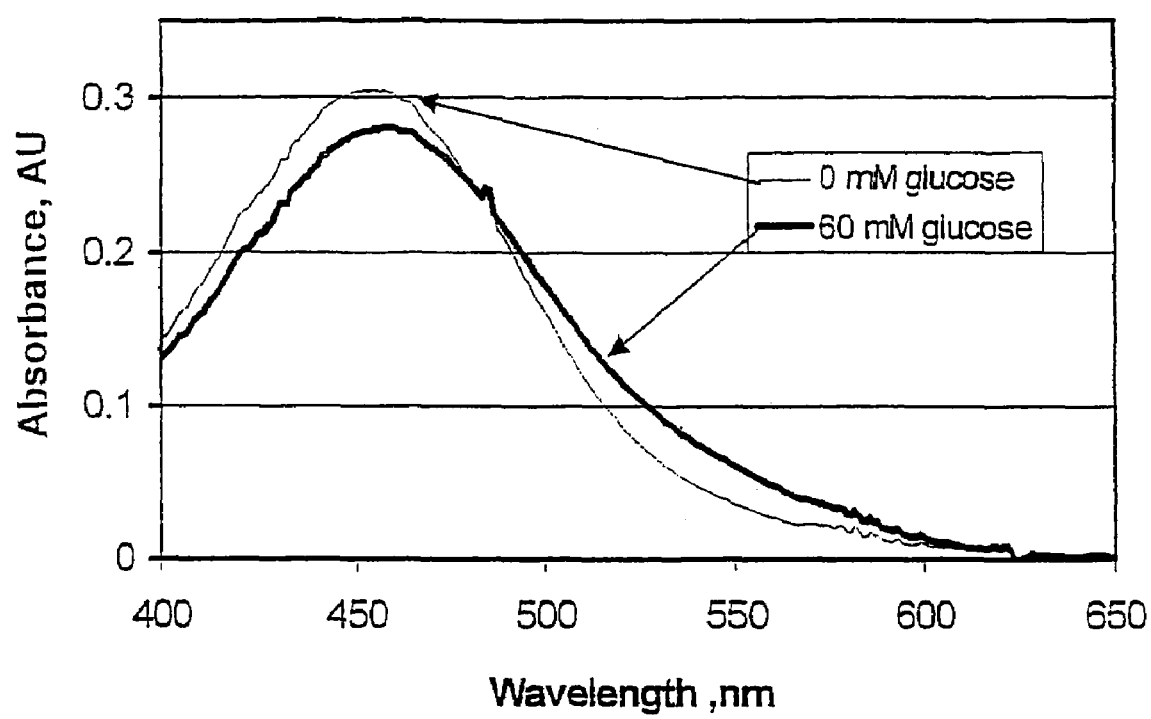
FIG. 6 illustrates the absorbance spectra of an indicator as described in Example 6.
Figure 7:
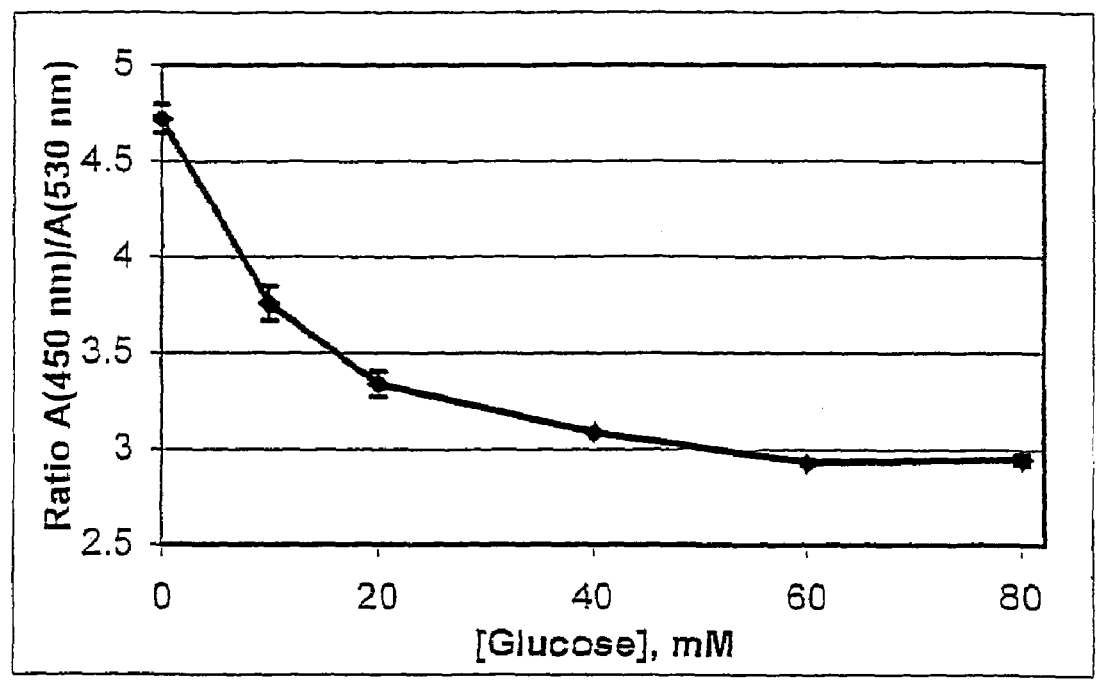
FIGS. 7–8 illustrate the ratio of the absorbance (450 nm/530 nm) of an indicator as described in Example 6.
Figure 8:
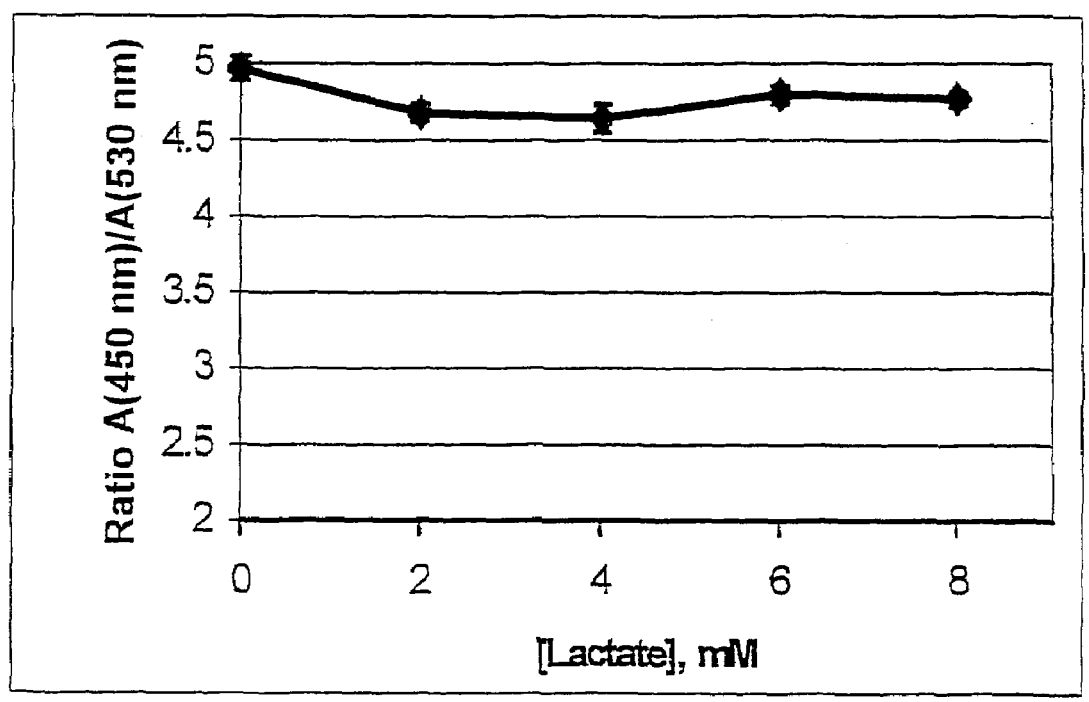

FIG. 6 shows the absorbance spectra for acrylamide gel (30%) containing 4 mM Alizarin Red S monomer and 44 mM bis boronic acid monomer with and without glucose. FIG. 7 shows the effect of glucose on absorbance of acrylamide gel (30%) containing 4 mM Alizarin Red S monomer and 44 mM bis boronic acid monomer. FIG. 8 shows the effect of sodium lactate on absorbance of acrylamide gel (30%) containing 4 mM Alizarin Red S monomer and 44 mM bis boronic acid monomer. The absorbance of the indicator was affected by the presence of glucose, but not substantially affected by the presence of lactate.

G. Modulation of Fluorescence with Glucose and Lactate

The modulation of the fluorescence of an acrylamide gel synthesized substantially in accordance with this Example 6 (except that 1.9 mg of N-[3-(methacrylamido)-propyl]-3,4-dihydroxy-9,10-dioxo-2-anthracenesulfonamide and 35 mg of α,α'-bis[N-[2-(5,5-dimethyl[1,3,2]dioxaborinan-2-yl)-benzyl]-N-[3-(methacrylamido)propylamino]-1,4-xylene were used) was determined.

Figure 9:
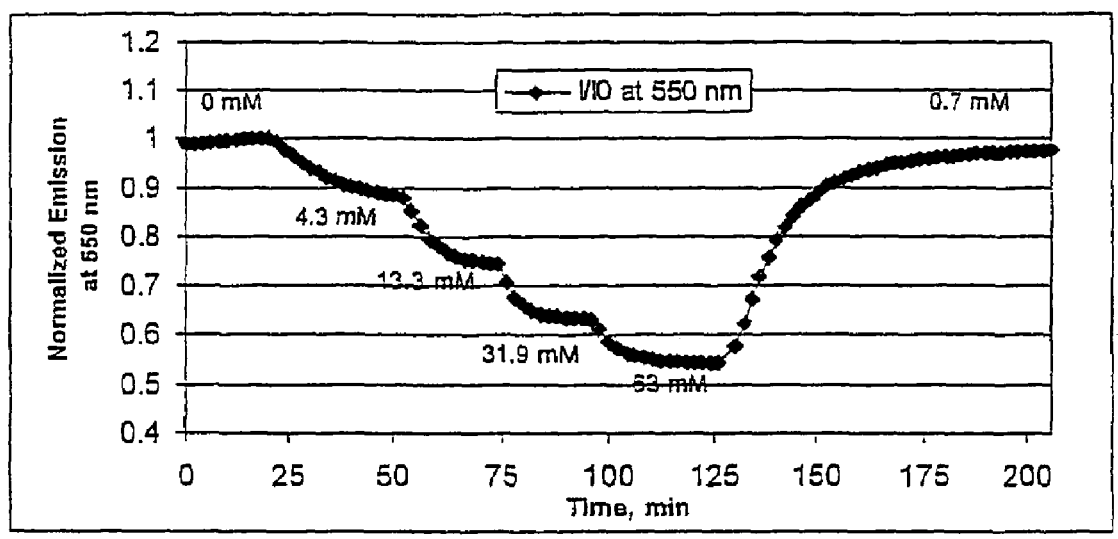
FIG. 9 illustrates the normalized fluorescence emission ($I/I_0$ at 550 nm) of an indicator as described in Example 6.
Figure 10:
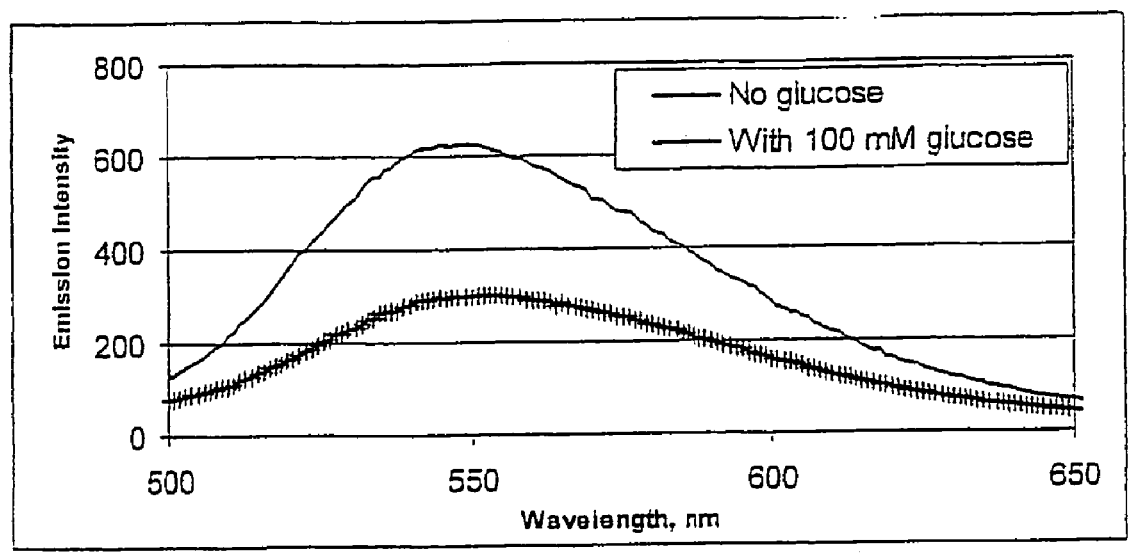
FIG. 10 illustrates the fluorescence spectrum, in the absence of glucose and in the presence of 100 mM glucose, of an indicator as described in Example 6.

The experiment was conducted in a Shimadzu RF-5301 PC spectrofluorimeter equipped with a variable temperature attachment (excitation at 470 nm, slits 3/10 nm, high sensitivity). The acrylamide gel was attached to a piece of a glass slide which was glued in a PMMA fluorescence cell at a 45° angle. The cell was filled with 2.5 ml of PBS (pH=7.4) and heated to 37° C. Stock solutions of glucose (100 mM and 500 mM) in PBS (pH=7.4) were prepared and heated to 37° C. in a water bath. An aliquot of heated glucose stock solution was added to the PMMA cell periodically while the fluorescence intensity at 550 nm was monitored as a function of time (1 measurement every 2 minutes). Glucose concentration in the PMMA cell was measured using a YSI Model 2300 STAT plus glucose analyzer. The results, shown in FIG. 9, show that the addition of glucose reduces the fluorescent intensity of the indicator hydrogel. The same effect is seen in FIG. 10, which shows the effect of glucose on the fluorescence spectrum of the same type of gel.

That effect is believed to occur because of the following considerations. The methacrylamide monomer of Alizarin Red S (reporter molecule) contains a vicinal diol functionality and monomer functionality (see structure below). In aqueous solution and in organic solvents, the Alizarin Red S and bis-boronate recognition element monomers (see structure below) are capable of reversible reaction with each other to form a boronate ester. The boronate ester molecule formed in this reversible reaction is fluorescent, while the Alizarin Red S monomer by itself displays virtually no fluorescence emission in aqueous solution and in organic solvents, such as MeOH. Thus upon binding to the glucose recognition element, Alizarin Red S changes its optical properties, such as absorbance and quantum yield of fluorescence, for example.

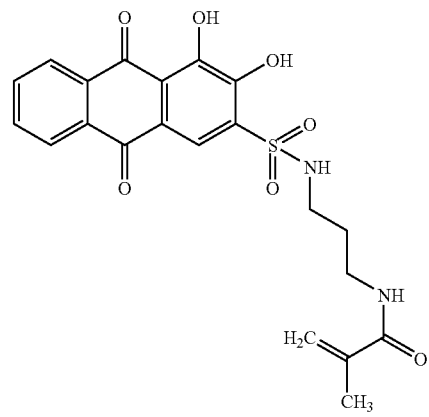

Alizarin Red S with monomer functionality

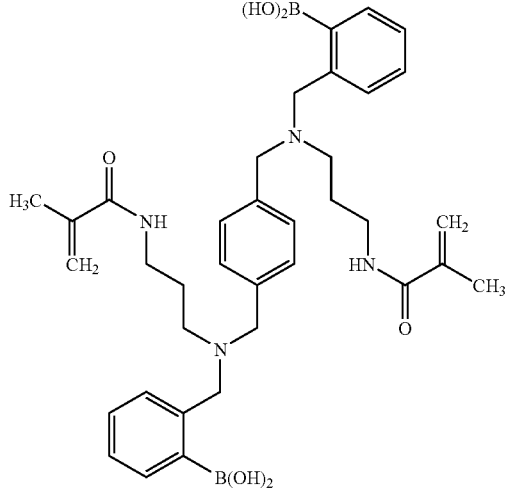

Recognition element with monomer functionality

A solution of Alizarin Red S with monomer functionality and glucose recognition element with monomer functionality can be prepared together with a hydrogel monomer and a crosslinker. Copolymerization of this mixture produces a hydrogel material which is diffusable to various small and medium size molecules; thus it is capable of analyte detection and quantitation. An analyte, such as glucose for example, would diffuse inside the hydrogel matrix and displace the reporter molecule previously bound to the recognition element. This event causes a change in the optical properties of the hydrogel film since it now contains a greater number of reporter molecules unbound to the recognition element.

Figure 11:
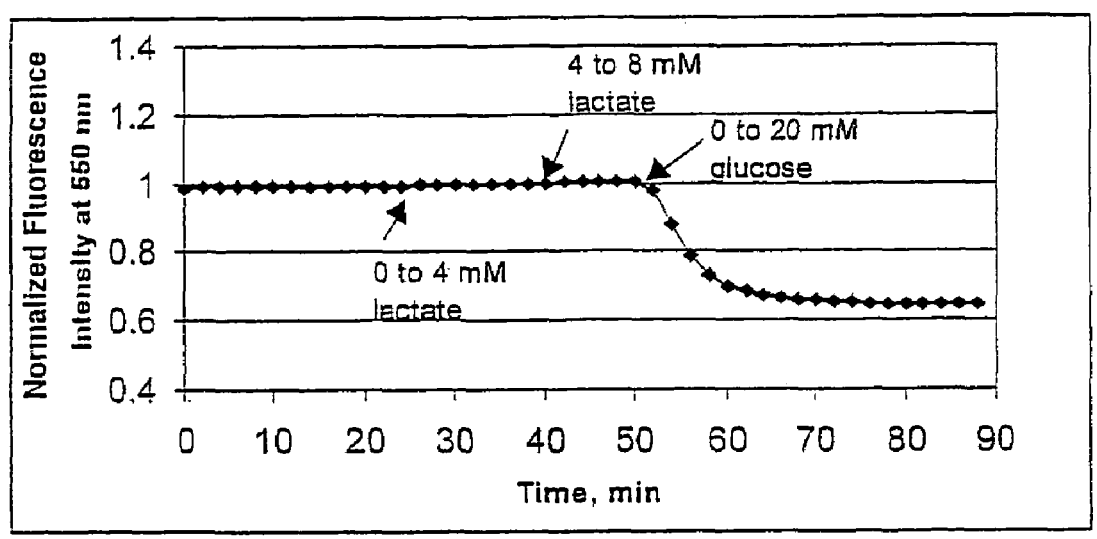
FIG. 11 illustrates the normalized fluorescence emission ($I/I_0$ at 550 nm), in the presence of glucose and lactate, of an indicator as described in Example 6.

The modulation of the fluorescence of the indicator compound (which contains two recognition elements) prepared in this example by glucose and lactate was also determined. The experiment was conducted in a Shimadzu RF-5301 PC spectrofluorimeter equipped with a variable temperature attachment (excitation at 470 nm, slits 5/10 nm, low sensitivity). The acrylamide gel was attached to a piece of a glass slide which was glued in a PMMA fluorescence cell at a 45° angle. The cell was filled with 2.5 ml of PBS (pH=7.4) and heated to 37° C. in a water bath. A stock solution of sodium lactate (100 mM) in PBS (pH=7.4) was prepared and heated to 37° C. in a water bath. Stock solutions of glucose (100 mM and 500 mM) in PBS (pH=7.4) were prepared and heated to 37° C. in a water bath. An aliquot of heated lactate stock solution was added to the PMMA cell periodically while the fluorescence intensity at 550 nm was monitored as a function of time (1 measurement every 2 minutes), until the lactate concentration reached 8 mM. Then, an aliquot of heated glucose stock solution was added to the PMMA cell periodically while the fluorescence intensity at 550 nm was monitored as a function of time (1 measurement every 2 minutes). Glucose concentration in the PMMA cell was measured using a YSI Model 2300 STAT plus glucose analyzer. The results, shown in FIG. 11, show that the addition of lactate had no significant effect on the fluorescent intensity of the indicator hydrogel, and the subsequent addition of glucose reduced the fluorescent intensity of the indicator hydrogel.

EXAMPLE 7

Single-Methacrylamide Monomer of bis-boronate-anthracene:

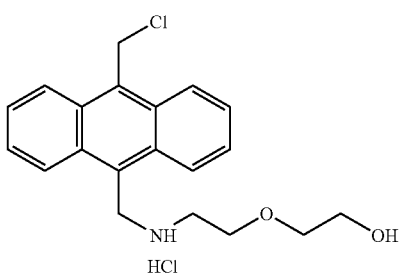

A. 9-chloromethyl-10-[[2-(2-hydroxyethoxy)ethylamino]-methyl]anthracene Hydrochloride Salt.

To a suspension of 9,10-bis(chloromethyl)anthracene (5.18 g, 18.8 mmole, 3.99 equiv.) in 200 mL of NMP was added 2-(2-aminoethoxy)ethanol (0.495 g, 0.475 mL, 4.71 mmole). The mixture was stirred in the dark for 17 hours. At this time, the reaction mixture was concentrated to ~50 mL under vacuum at 50° C. The residue was purified by silica gel chromatography (150 g gravity grade silica gel, 0–10% $CH_3OH/CH_2Cl_2$) to yield 0.425 g (24%) of a yellow/orange solid.

TLC: Merck silica gel 60 plates, Rf 0.72 with 70/30 $CH_2Cl_2/CH_3OH$, see with UV (254/366), ninhydrin stain.

HPLC: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 16.1 min.

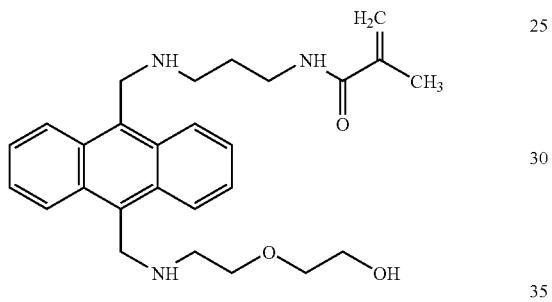

B. 9-[[2-(2-hydroxyethoxy)ethylamino]methyl]-10-[[(3-methacrylamido)propylamino]methyl]-anthracene.

To a suspension of N-(3-aminopropyl)methacrylamide hydrochloride salt (3.08 g, 17.2 mmole, 4.2 equiv.), DIEA (5.19 g, 7.00 mL, 40.1 mmole, 9.8 equiv.) and ~3 mg of BHT in 125 mL $CHCl_3$ at 23° C. was added dropwise a solution of 9-chloromethyl-10-[[2-(2-hydroxyethoxy)ethylamino]-methyl]anthracene hydrochloride salt (1.56 g, 4.10 mmole) in 25 mL of $CHCl_3$. The mixture was subsequently stirred in the dark for 92 hours. At this time, the reaction mixture was filtered and washed with 2×40 mL of $NaHCO_3$ (saturated aqueous solution). The organic extract was dried over anhydrous $Na_2SO_4$, filtered and concentrated to yield a sticky orange solid which was purified by alumina chromatography (50 g activated neutral alumina, 0–5% $CH_3OH/CH_2Cl_2$) to yield 0.364 g (20%) of an orange solid.

TLC: Merck silica gel 60 plates, Rf 0.16 with 70/30 $CH_2Cl_2/CH_3OH$, see with UV (254/366), ninhydrin stain HPLC: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 16.85 min.

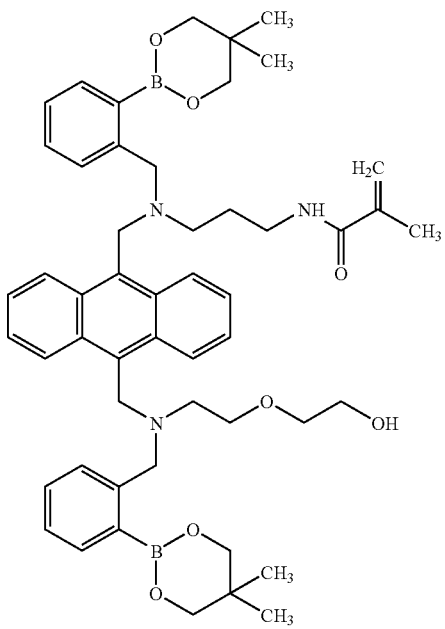

C. 9-[N-[2-(5,5-dimethyl[1,3,2]dioxaborinan-2-yl)benzyl]-N-[3-(methacrylamido)propylamino]methyl]-10-[N-[2-(5,5-dimethyl[1,3,2]dioxaborinan-2-yl)benzyl]-N-[2-(2-hydroxyethoxy)-ethylamino]methyl]anthracene. (Single-methacrylamide monomer)

A solution of 9-[[2-(2-hydroxyethoxy)ethylamino]-methyl]-10-[[(3-methacrylamido)propylamino]methyl]-anthracene (0.343 g, 0.763 mmole), DIEA (0.965 g, 1.30 mL, 9.8 equiv.) and (2-bromomethylphenyl)boronic acid neopentyl ester (1.09 g, 3.85 mmole, 5.0 equiv.) in 20 mL $CHCl_3$ at 23° C. was stirred in the dark for 25 hours. At this time, the reaction mixture was concentrated initially by rotary evaporation, then using a vacuum pump to remove DIEA. The residue was purified by alumina column chromatography (40 g activated neutral alumina, 0–10% $CH_3OH/CH_2Cl_2$) to yield 0.299 g (46%) of a yellow orange solid. This compound may be co-polymerized with a suitable monomer as described previously, deprotected, and used to detect glucose.

FAB MS: Calc=d for $C_{51}H_{65}B_2N_3O_7$ [M]$^+$ 854. Found [M+1]$^+$ 855.

TLC: Merck basic alumina plates, Rf 0.35 with 95/5 $CH_2Cl_2/CH_3OH$, see with UV (254/366).

HPLC: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 19.7 min.

EXAMPLE 8

Dual-methacrylate Monomer of bis-boronate-anthracene

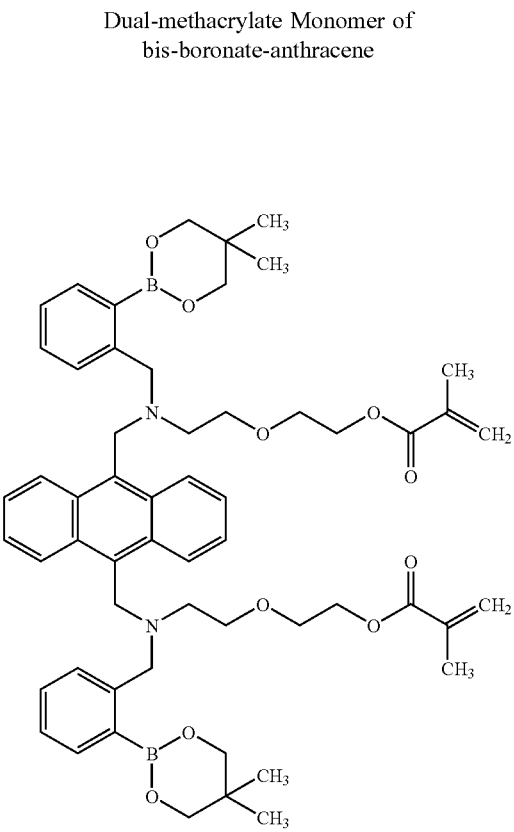

A. 9,10-bis[N-[2-(5,5-dimethyl[1,3,2]dioxaborinan-2-yl)benzyl]-N-[2-(2-methacroyloxyethoxy)ethylamino]methyl] anthracene.

A solution of 9,10-bis[N-[2-(5,5-dimethyl[1,3,2]dioxaborinan-2-yl)benzyl]-N-[2-(2-hydroxyethoxy)ethylamino]methyl]-anthracene (0.100 g, 0.120 mmole; see Example 2), methacrylic acid (0.112 g, 0.110 mL, 1.30 mmole, 10.8 equiv.), DCC (0.316 g, 1.53 mmole, 12.8 equiv.) and N,N-dimethylamino-pyridine (0.014 g, 0.11 mmole, 0.92 equiv.) in 5 mL $CH_2Cl_2$ was stirred at 0° C. for 1 hour, then 23° C. for 22 hours. At this time, the reaction mixture was filtered and concentrated by rotary evaporation. The residue was purified by alumina column chromatography (30 g activated neutral alumina, 0–2% $CH_3OH/CH_2Cl_2$) to yield 0.030 g (26%) of a yellow solid. This compound may be co-polymerized with a suitable monomer as described previously, deprotected, and used to detect glucose.

FAB MS: Calc=d for $C_{56}H_{70}B_2N_2O_{10}$ $[M]^+$ 953. Found $[M]^+$ 951 (weak molecular ion peak).

TLC: Merck basic alumina plates, Rf 0.67 with 95/5 $CH_2Cl_2/CH_3OH$, see with UV (254/366).

HPLC: HP 1100 HPLC chromatograph, Waters 5×100 mm NovaPak HR C18 column, 0.100 mL injection, 0.75 mL/min, 2 mL injection loop, 370 nm detection, A=water (0.1% HFBA) and B=MeCN (0.1% HFBA), gradient 10% B 2 min, 10–80% B over 18 min, 80–100% B over 2 min, 100% B 2 min, retention time 19.6 min.

EXAMPLE 9

Dual 5-aminopentyl bis-boronate-anthracene

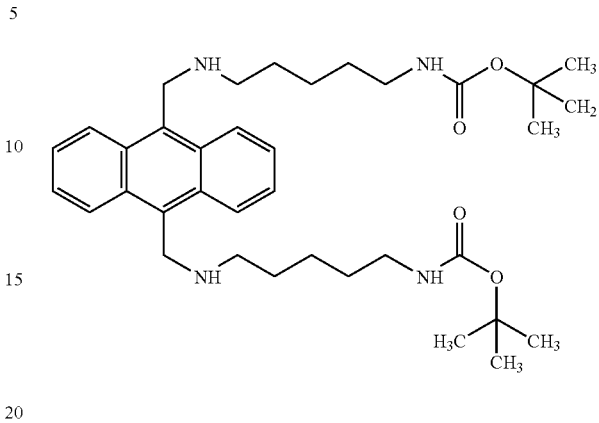

A. 9,10-bis[[5-(t-BOC)-aminopentylamino]methyl]-anthracene.

A suspension of 9,10-bis(chloromethyl)anthracene (0.28 g, 1 mmole), DIEA (7.0 mL, 40 mmole), mono-t-butoxycarbonyl 1,5-diaminopentane (3.75 g, 10 mmole), and 50 ml of $CHCl_3$ was stirred in the dark for 2 days at 45° C. The solution was washed with saturated $H_2O/NaHCO_3$, the organic phase was dried ($Na_2SO_4$), and the solvent was evaporated. The residue was purified by alumina chromatography (40 g activated neutral alumina, 95/5% vol. $CH_2Cl_2/MeOH$) to yield 0.55 g of viscous oil. This material was used as is for the next step.

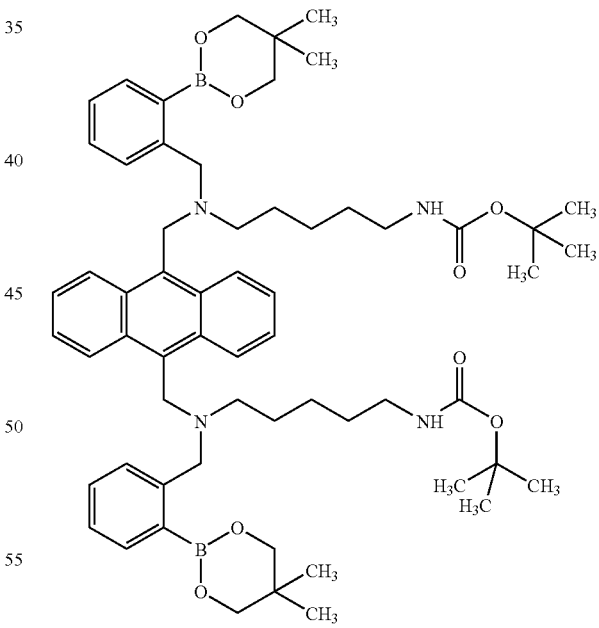

B. 9,10-bis[N-[2-(5,5-dimethyl[1,3,2]dioxaborinan-2-yl)benzyl]-N-[5-(t-BOC)-aminopentylamino]methyl]anthracene.

A solution of 9,10-bis[[5-(t-BOC)-aminopentylamino]methyl]anthracene (0.3 g, 0.49 mmole), DIEA (0.35 mL, 2 mmole), and (2-bromomethylphenyl)boronic acid neopentyl ester (0.566 g, 2.0 mmole) in 20 mL $CH_2Cl_2$ was stirred in the dark for 2 days at 25° C. At this time, the reaction mixture was concentrated in vacuo and the residue was purified by alumina chromatography (60 g of activated neutral alumina, 98/2% vol. CH$_2$Cl$_2$/MeOH) to yield 0.401 g of yellow oil. This material was used as is for the next step.

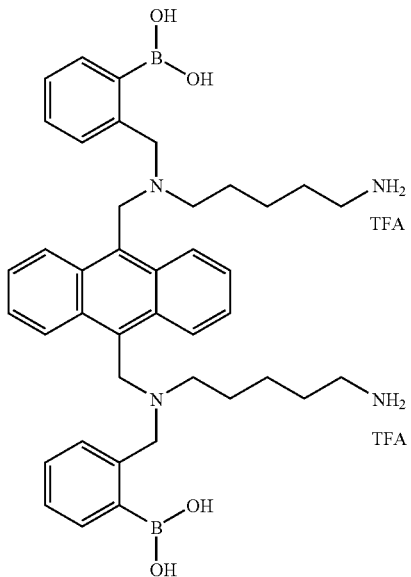

C. 9,10-bis[N-(2-boronobenzyl)-N-[5-aminopentylamino]-methyl]anthracene trifluoroacetic acid salt.

9,10-bis[N-[2-(5,5-dimethyl[1,3,2]dioxaborinan-2-yl)benzyl]-N-[5-(t-BOC)-aminopentylamino]methyl]anthracene (0.4 g, 0.39 mmole) was dissolved in 20 ml of CH$_2$Cl$_2$/TFA (80/20% vol.). The solution was stirred for 12 hours, the solvent was evaporated, and the residue was washed with 10 ml of ether. A total of 373 mg of solid was obtained (72% yield). Product was ~80% pure by RP-HPLC. This compound may be co-polymerized with a suitable monomer as described previously, deprotected, and used to detect glucose.

HPLC: HP 1100 HPLC chromatograph, Waters 5×100 mm NovaPak HR C18 column, 0.050 mL injection, 0.75 mL/min, 360 nm detection, A=water (0.1% HFBA) and B=MeCN (0.1% HFBA), gradient 10% B 2 min, 10–80% B over 18 min, 80–100% B over 2 min, 100% B 2 min, retention time 16.0 min.

EXAMPLE 10

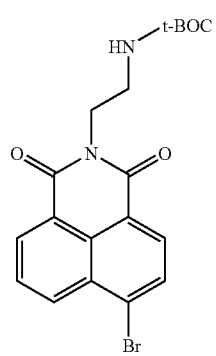

A. N-2-(tert-butoxycarbonyl)aminoethyl-4-bromonaphthalene-1,8-dicarboximide:

N-t-Boc-ethylenediamine (Fluka, 1.6 g, 10 mmole) and 4-bromo-1,8-naphthalic anhydride (Aldrich, 2.77 g, 10 mmole) were combined with 60 ml of anhydrous ethanol, the suspension was stirred at 60° C. for 20 hours, cooled to room temperature, and filtered. The obtained solid was washed with 30 ml of cold EtOH and dried under vacuum. Yield 3.84 g (91%). NMR (CDCl3): 1.28 (9H, s); 3.52 (2H, t); 4.35 (2H, t); 4.92 (1H, s);7.84 (1H, t); 8.04 (1H, d); 8.42 (1H, d); 8.58 (1H, d); 8.67 (1H, d).

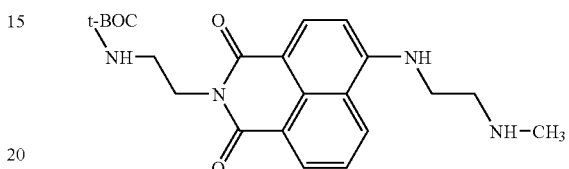

B. N-2-(tert-butoxycarbonyl)aminoethyl-4-(N'-methylaminoethylamino)naphthalene-1,8-dicarboximide:

N-Methylethylenediamine (1.48 g, 20 mmole) was combined with 2 ml of 1-methyl-2-pyrrolidinone (NMP) followed by addition of N-2-(tert-butoxycarbonyl)aminoethyl-4-bromonaphthalene-1,8-dicarboximide (0.35 g, 0.845 mmole). The resulting solution was stirred at 45° C. for 40 hours after which NMP and N-methylethylenediamine were evaporated under vacuum. The obtained residue was subjected to column chromatography (20 g of silica gel, initially CH$_2$Cl$_2$/MeOH (90/10), then CH$_2$Cl$_2$/MeOH/Et$_3$N (75/20/5)). A yellow solid was obtained (0.311 g, 89% yield). Purity was checked by RP-HPLC.

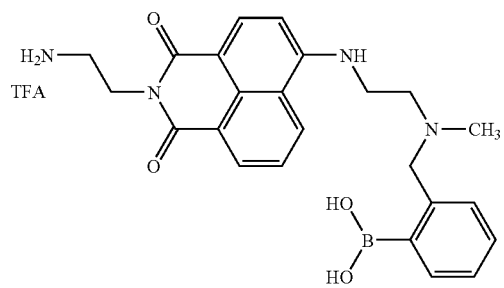

C. N-aminoethyl-4-(N'-aminoethylene-N''-[2-(borono)benzyl]methylamino)naphthalene-1,8-dicarboximide trifluoroacetic acid salt:

N-2-(tert-butoxycarbonyl)aminoethyl-4-(N'-methylaminoethylamino)naphthalene-1,8-dicarboximide (0.3 g, 0.73 mmole), 2-bromomethylphenyl boronic acid, pinacol ester (0.6 g, 2 mmole), N,N-diisopropyl-N-ethylamine (1.3 ml, 8 mmole), and 10 ml of CH$_2$Cl$_2$ were combined. The solution was stirred for 20 hours, followed by addition of 2 g of PS-Trisamine resin (Argonaut Technologies, 3.38 mmol/g). The reaction mixture and resin were agitated for 10 hours after which the resin was removed by filtration and washed with CH$_2$Cl$_2$ (2×20 ml). Combined CH$_2$Cl$_2$ solutions were evaporated and dried under vacuum.

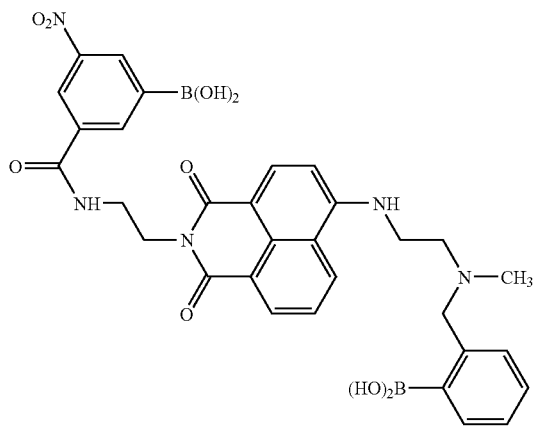

Methylene chloride solution containing 20% vol. TFA and 5% vol. triisopropyl silane was added to the resulting orange residue. The resulting solution was stirred at room temperature for 10 hours, after which the solvent was evaporated and the residue triturated with ether to yield a yellow solid. The solid was filtered and dried in vacuum (yield 580 mg). Purity of the material was checked by RP-HPLC. The solid was used as is in the next step.

D. N-(3-Borono-5-nitrobenzamido)ethyl-4-(N'-aminoethylene-N"-[2-(borono)benzyl]methylamino)naphthalene-1,8-dicarboximide:

N-aminoethyl-4-(N'-aminoethylene-N"-[2-(borono)benzyl]methylamino)naphthalene-1,8-dicarboximide trifluoroacetic acid salt (0.225 g, 0.4 mmole), 3-carboxy-5-nitrophenylboronic acid (0.085 g, 0.4 mmole), diphenylphosphoryl azide (0.13 ml, 0.6 mmole), and 2 ml of anhydrous DMF were combined. N,N-diisopropyl-N-ethyl amine (0.7 ml, 4 mmole) was added and the solution was stirred for 20 hours. Ether (10 ml) was added to the reaction mixture and the insoluble residue was separated and sonicated with 5 ml of $CH_2Cl_2$ to yield an orange solid which was filtered and dried under vacuum (38 mg, 15% yield). Purity of the solid was checked by RP-HPLC. NMR (dmso-d6/D2O, 90/10): δ 2.32 (3H, s); 2.82 (2H, t); 3.58 (2H, t); 3.65 (2H, t), 3.70 (2H, s); 6.65 (1H, d); 7.0–7.3 (4H, m); 7.68 (1H, t); 8.18 (1H, d); 8.42 (1H, d); 8.47 (1H, d); 8.1–8.35 (3H, m).

E. Test of N-(3-borono-5-nitrobenzamido)ethyl-4-(N'-aminoethylene-N"-[2-(borono)benzyl]methylamino)naphthalene-1,8-dicarboximide for interaction with glucose as monitored by fluorescence This experiment was conducted in MeOH/phosphate buffered saline, (PBS, 10 mM, pH=7.4). The concentration of N-(3-borono-5-nitrobenzamido)ethyl-4-(N'-aminoethylene-N"-[2-(borono)benzyl]methylamino)naphthalene-1,8-dicarboximide in MeOH/PBS, (50/50 vol. %) was 15 M. The glucose concentration was varied from 0 mM to 50 mM, and the L-sodium lactate concentration was varied from 0 mM to 7 mM. The experiment was conducted in a Shimadzu RF-5301 PC spectrofluorimeter: excitation wavelength was set at 430 nm, emission was monitored in the 480–650 nm range, slit width 3/1.5 nm, high sensitivity of PMT.

Figure 12:
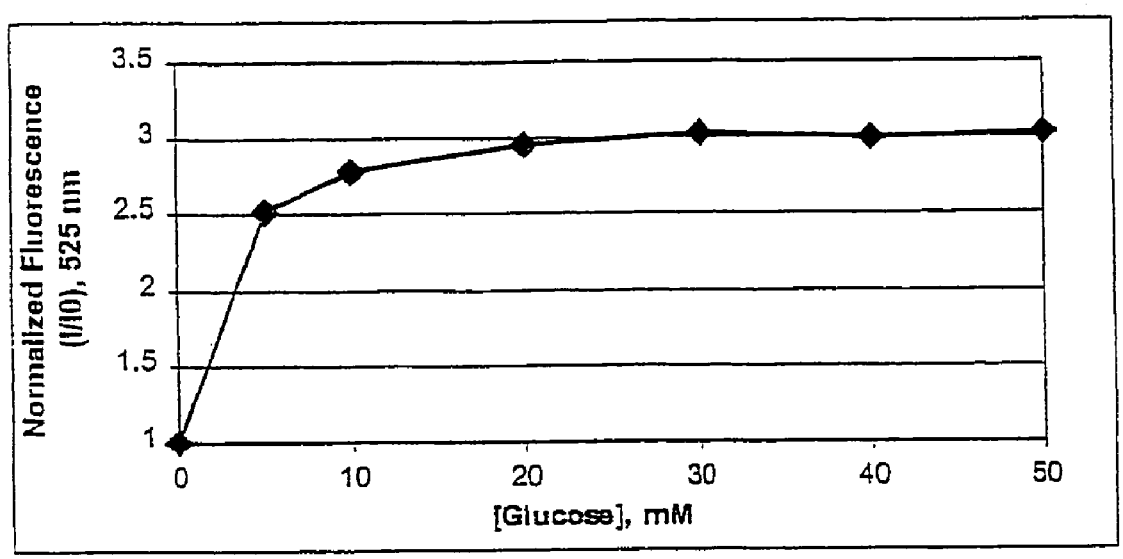
FIG. 12 illustrates the normalized fluorescence emission ($I/I_0$ at 525 nm) of an indicator exposed to glucose as described in Example 10.
Figure 13:
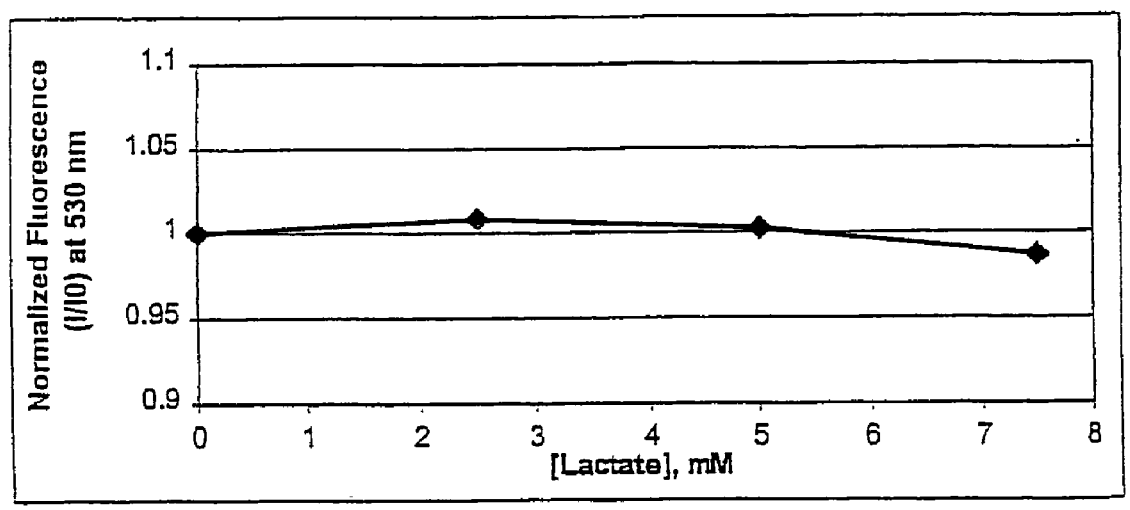
FIG. 13 illustrates the normalized fluorescence emission ($I/I_0$ at 530 nm) of an indicator exposed to lactate as described in Example 10.

The results are shown in FIGS. 12 and 13, which show that the fluorescence of the indicator of this example was affected by the presence of glucose, but not by the presence of lactate.

EXAMPLE 11

6-(Cyclohexanecarboxamido)hexylamine Indicator Monomer

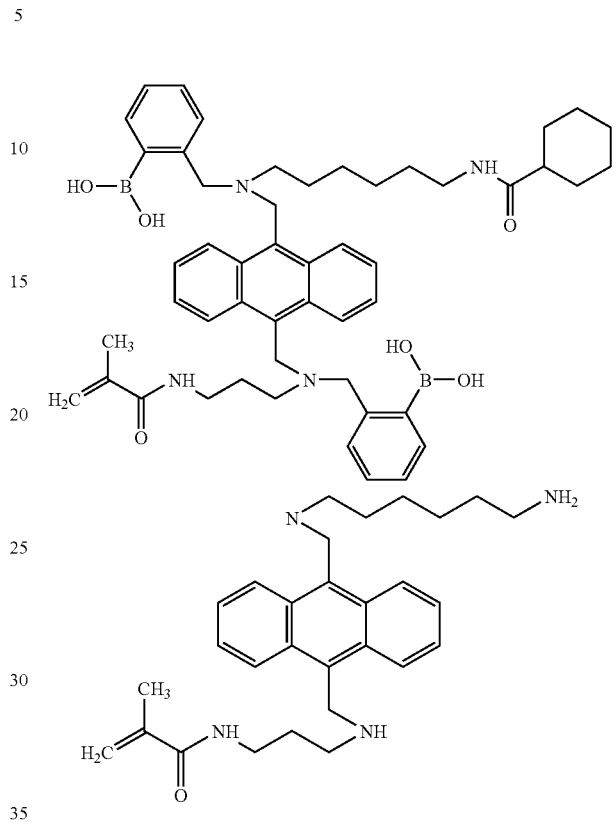

A.  9-[N-[3-(methacrylamido)propylamino]methyl]-10-N-[(6-aminohexylamino)methyl]anthracene.

To a solution of 3-aminopropylmethacrylamide (0.775 g, 5.45 mmol, 10.0 equiv.) and tert-butyl N-(6-aminohexyl) carbamate (1.18 g, 5.45 mmol, 10.0 equiv.) and several crystals of BHT in 200 mL $CHCl_3$ was added 9,10-bis (chloromethyl)anthracene (0.150 g, 0.545 mmol). The reaction mixture was subsequently stirred in the dark at ambient temperature for 4 days. At this time, the $CHCl_3$ was evaporated and the residue was dissolved in 100 mL ether. The organic layer was extracted with 8×125 mL sat'd aqueous $NaHCO_3$ and 5×200 mL phosphate buffer (0.4 M, pH 7.0). The pH of the combined phosphate buffer washes was adjusted to pH 11 by addition of $Na_2CO_3$ (sat'd aqueous solution), followed by extraction with 5×300 mL $CH_2Cl_2$. The combined organic layers were concentrated and the residue dissolved in 5 mL of a 20% solution of TFA in $CH_2Cl_2$. The mixture was stirred at ambient temperature for 2 hours. At this time, the reaction mixture was extracted with 4×10 mL sat'd aqueous $NaHCO_3$. The pH of the combined aqueous layers was adjusted to pH 11 by addition of $Na_2CO_3$ (sat'd aqueous solution), followed by extraction with 4×75 mL $CH_2Cl_2$. The combined organic extracts were dried over anhydrous $Na_2SO_4$, filtered and concentrated in vacuo to yield 0.068 g (27%) of product.

TLC: a) Merck Silica Gel 60 plates, Rf 0.16 with 70/30 $CH_2Cl_2/CH_3OH$, see with UV (254/366), prior to deprotection; Rf 0.27 with 85/14.5/0.5 $CH_2Cl_2/CH_3OH/iPrNH_2$, see with UV (254/366), final product.

HPLC: HP 1100 HPLC chromatograph, Waters 8×100 mm NovaPak HR C18 column, 0.100 mL injection, 0.75 mL/min, 0.400 mL injection loop, 360 nm detection, A=water (0.1% HFBA) and B=MeCN (0.1% HFBA), gradient 10% B 2 min, 10–80% B over 18 min, 80–100% B over 2 min, 100% B 2 min, retention time 15.5 min.

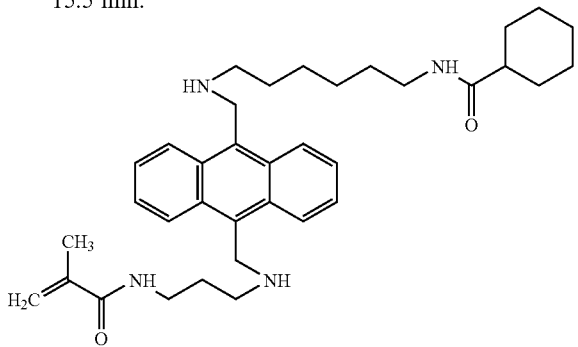

B. 9-[N-[3-(methacrylamido)propylamino]methyl]-10-[N-[6-(cyclohexanecarboxamido)hexylamino]methyl]anthracene.

To a solution of 9-[N-[3-(methacrylamido)propylamino]methyl]-10-N-[6-aminohexylamino)methyl]anthracene (1.68 g, 3.63 mmol) and a few crystals of BHT in 20 mL CH$_2$Cl$_2$ at ambient temperature was added dropwise a solution of cyclohexanecarboxylic acid N-hydroxysuccinimide ester (0.845 g, 3.76 mmol, 1.03 equiv.) over a 1 hour period. The reaction was subsequently stirred in the dark at ambient temperature for 16 hours. At this time, the reaction mixture was concentrated in vacuo and the residue dissolved in 105 mL of a solution of 90/15 ether/CH$_2$Cl$_2$. The organic layer was extracted with 4×225 mL phosphate buffer (0.4 M, pH 7.0). The pH of the combined phosphate buffer washes was adjusted to pH 11 by addition of Na$_2$CO$_3$ (sat'd aqueous solution), followed by extraction with 6×500 mL CH$_2$Cl$_2$. The combined organic layers were dried over anhydrous Na$_2$SO$_4$, filtered and concentrated in vacuo to yield 1.2 g (60%) of product.

TLC: Merck Silica Gel 60 plates, Rf 0.30 with 85/14.5/0.5 CH$_2$Cl$_2$/CH$_3$OH/iPrNH$_2$, see with UV (254/366)

HPLC: HP 1100 HPLC chromatograph, Waters 8×100 mm NovaPak HR C18 column, 0.100 mL injection, 0.75 mL/min, 0.400 mL injection loop, 360 nm detection, A=water (0.1% HFBA) and B=MeCN (0.1% HFBA), gradient 10% B 2 min, 10–80% B over 18 min, 80–100% B over 2 min, 100% B 2 min, retention time 17.4 min.

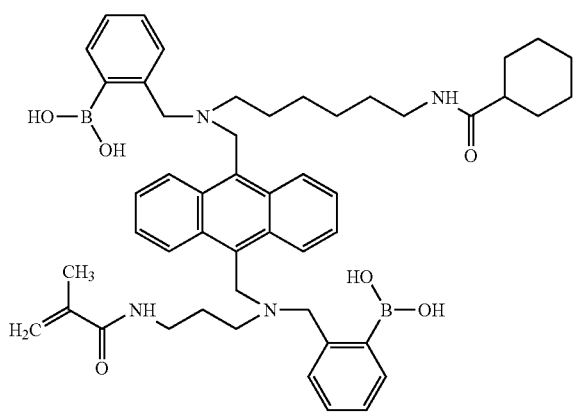

C. 9-[N-(2-boronobenzyl)-N-[3-(methacrylamido)propylamino]methyl]-10-[N-(2-boronobenzyl)-N-[6-(cyclohexanecarboxamido)hexylamino]-methyl]anthracene.

A solution of 9-[N-[3-(methacrylamido)propylamino]methyl]-10-[N-[6-(cyclohexanecarboxamido)hexylamino]methyl]-anthracene (1.0 g, 1.8 mmol), DIEA (1.81 g, 2.44 mL, 14.0 mmol, 7.8 equiv.), 2-bromomethylphenylboronic acid pinacol ester (2.14 g, 7.20 mmol, 4.0 equiv.) and a few crystals of BHT in 30 mL CHCl$_3$ was stirred in the dark at ambient temperature for 60 hours. At this time, the reaction mixture was concentrated and the residue (9-[N-[2-(4,4,5,5,-tetramethyl-1,3,2-dioxaborolano)benzyl]-N-[3-(methacrylamido)propylamino]methyl]-10-[N-[2-(4,4,5,5,-tetramethyl-1,3,2-dioxaborolano)benzyl]-N-[6-(cyclohexanecarboxamido)hexylamino]methyl]anthracene) suspended in 150 mL ether. The organic layer was washed with 4×50 mL phosphate buffer (0.4 M, pH 7.0). The organic layer was concentrated and the residue dissolved in ether in 200 mL 0.1 N aqueous HCl. The aqueous layer was washed with 3×50 mL 1:1; ether:ethyl acetate and the pH was adjusted to pH 11 by addition of Na$_2$CO$_3$ (sat'd aqueous solution), followed by extraction with 3×150 mL CH$_2$Cl$_2$. The combined organic layers were dried over anhydrous Na$_2$SO$_4$, filtered and concentrated in vacuo to yield a red oily compound. The residue was dissolved in ether and concentrated in vacuo to yield 1.17 g (85%) of a yellow solid product.

TLC: Merck Silica Gel 60 plates, Rf 0.59 with 80/20 CH$_2$Cl$_2$/CH$_3$OH, see with UV (254/366)

HPLC: HP 1100 HPLC chromatograph, Waters 8×100 mm NovaPak HR C18 column, 0.100 mL injection, 0.75 mL/min, 0.400 mL injection loop, 360 nm detection, A=water (0.1% HFBA) and B=MeCN (0.1% HFBA), gradient 10% B 2 min, 10–80% B over 18 min, 80–100% B over 2 min, 100% B 2 min, retention time 19.6 min.

$^1$H NMR (9:1 d$_6$-acetone/D$_2$O): δ 0.90 (m, 2H), 1.03 (m, 2H), 1.18–1.30 (m, 6H), 1.35–1.48 (4H), 1.62 (m, 1H, O=C—CH(CH$_2$)CH$_2$), 1.66–1.75 (m, 7H), 1.77 (m, 2H, N—CH$_2$—CH$_2$—CH$_2$—N), 2.52 (m, 2H, N—CH$_2$—CH$_2$—), 2.63 (m, 2H, N—CH$_2$—CH$_2$—), 2.98 (m, 4H, —CH$_2$—NH—C=O), 3.98 (s, 4H, benzene-CH$_2$—N), 4.57 (s, 2H, athracene-CH$_2$—N), 4.59 (s, 2H, athracene-CH$_2$—N), 5.20 (t, 1H, J=1.5 Hz, C=CH$_2$), 5.46 (s, 1H, C=CH$_2$), 7.4–7.5 (m, 8H, Ar—H), 7.52 (m, 2H, Ar—H), 7.95 (m, 2H, Ar—H), 8.23 (m, 4H, Ar—H)

D. N,N-dimethylacrylamide hydrogel with 9-[N-(2-boronobenzyl)-N-[3-(methacrylamido) propylamino]methyl]-10-[N-(2-boronobenzyl)-N-[6-(cyclohexanecarboxamido) hexylamino]methyl]anthracene.

A solution of N,N-dimethylacrylamide (40% wt.) and N,N'-methylenebisacrylamide (0.8% wt.) in phosphate buffer, pH=7.4, 200 mM was prepared. 9-[N-(2-Boronobenzyl)-N-[3-(methacrylamido)propylamino]methyl]-10-[N-(2-boronobenzyl)-N-[6-(cyclohexanecarboxamido)hexylamino]methyl]anthracene (18 mg, 2.15×10$^{-5}$ mole) and 60 mg of fructose were combined with 2 mL of MeOH. This solution was sonicated until all of the fructose dissolved and was subsequently evaporated to yield a solid. To this solid, 1 mL of phosphate buffer solution containing monomers was added. After sonication for 10 min this solution was filtered through a 0.2 μM PTFE membrane filter. Aqueous ammonium persulfate (20 μL, 5% wt.) was combined with the formulation. The resulting solution was placed in glove box purged with nitrogen. An aqueous solution of N,N,N',N'-tetramethylethylenediamine (40 μL, 5% wt.) was added to the monomer formulation to accelerate polymerization. The resulting formulation was poured into a mold constructed from glass microscope slides and a 100 'M stainless steel spacer. After being kept for 8 hours in a nitrogen atmosphere, the mold was placed in phosphate buffered saline (pH=7.4), the microscope slides were separated, and the hydrogel was removed. The hydrogel was washed with 100 mL of phosphate buffered saline (PBS) containing 1 mM lauryl sulfate sodium salt and 1 mM EDTA tetrasodium salt for 3 days, the solution being changed every day, followed by washing with EtOH/PBS (20/80 by vol., 3×100 mL), and finally with PBS (H=7.4, 3×100 mL). The resulting hydrogel film was stored in PBS (pH=7.4) containing 0.02% wt. sodium azide and 1 mM EDTA tetrasodium salt.

E. Modulation of Fluorescence with Glucose.

Figure 14:
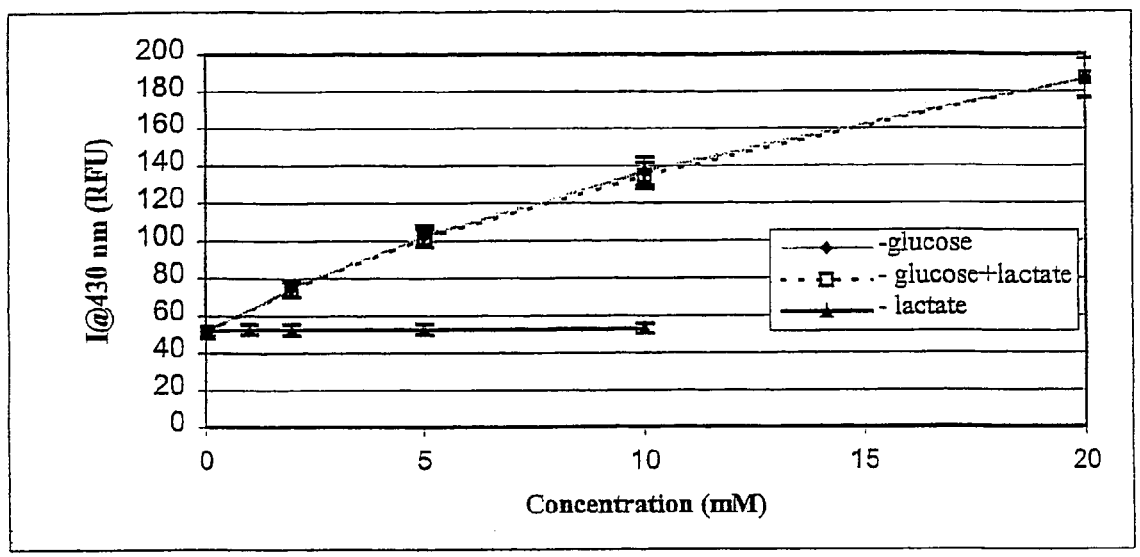
FIG. 14 shows the relative fluorescence emission (I @ 430 nm) of an indicator exposed to glucose and lactate as described in Example 11.

The modulation of the fluorescence of the 6-(cyclohexanecarboxamido)hexylamine indicator/DMA hydrogel film prepared in this example by glucose and lactate was determined. FIG. 14 shows the relative fluorescence emission (I @ 430 nm) of the hydrogel film in PBS (pH 7.4 containing 0.02% NaN$_3$ and 1 mM EDTA) containing 0 to 20 mM α-D-glucose, 0 to 10 mM L-sodium lactate, and 0–20 mM α-D-glucose in the presence of 4 mM L-sodium lactate. The hydrogel film (100 μm thickness, 8 mm diameter disk) was mounted in a PMMA cuvette at a 45° angle. All measurements were made at 37° C. in a Shimadzu RF-5301 spectrofluorometer with excitation at 370 nm (slit=3 nm) and emission at 430 nm (slit=3 nm) at low PMT sensitivity. Glucose and L-sodium lactate concentrations were checked using the YSI Model 2300 STAT plus glucose analyzer. Error bars are standard deviation with triplicate values for each data point. The fluorescence was affected by the presence of glucose, but not by the presence of lactate. Moreover, the presence of lactate (4 mM) had no significant effect on the 0–20 mM glucose calibration curve.

EXAMPLE 12

2-(carboxyethyl)amine Indicator Monomer

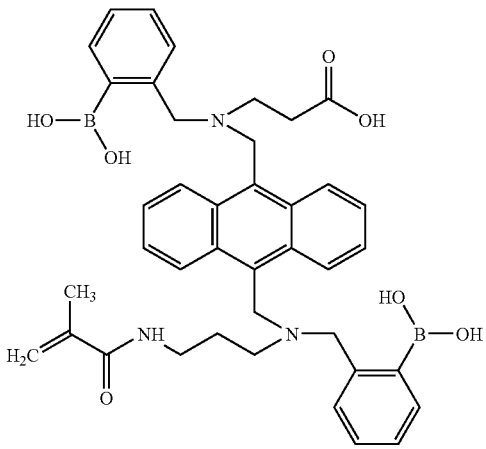

Chemical Name: 9-[N-(2-boronobenzyl)-N-[3-(methacrylamido)propylamino]methyl]-10-[N-(2-boronobenzyl)-N-[2-(carboxyethyl)amino]methyl]anthracene (uncapped)

Chemical Formula: C$_{40}$H$_{45}$B$_2$N$_3$O$_7$

MW: 701.4

Physical appearance: faint yellow powder

Solubility: PBS/methanol, methanol, ethanol, chloroform, dichloromethane

Capped Indicator: 9-[N-[2-(4,4,5,5,-tetramethyl-1,3,2-dioxaborolano)benzyl]-N-[3-(methacrylamido)propylamino]methyl]-10-[N-[2-(4,4,5,5,-tetramethyl-1,3,2-dioxaborolano)benzyl]-N-[2-(carboxyethyl)amino]methyl]anthracene.

I. Synthesis

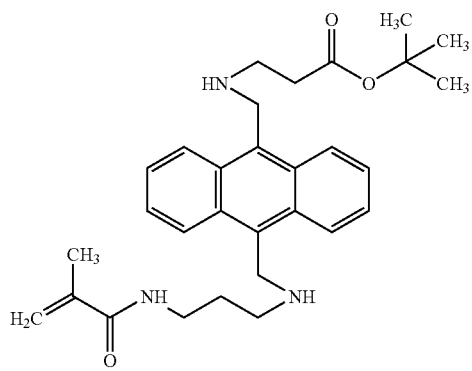

A. 9-[N-[3-(methacrylamido)propylamino]methyl]-10-[N-[2-(tert-butoxycarbonyl)ethylamino]methyl]anthracene.

To a solution of 3-aminopropylmethacrylamide (12.9 g, 90.7 mmol, 4.99 equiv.), β-alanine tert-butyl ester (13.2 g, 90.9 mmol, 5.00 equiv.) and several crystals of BHT in 700 mL CHCl$_3$ was added 9,10-bis(chloromethyl)anthracene (5.00 g, 18.2 mmol). The reaction mixture was subsequently stirred in the dark at 30° C. for 88 hours. At this time, the CHCl$_3$ was evaporated and the residue was dissolved in 500 mL ether. The solution was stirred for 1 hour at which time salts had precipitated from solution. The ether solution was filtered and subsequently extracted with 10×350 mL sat'd aqueous NaHCO$_3$. The ether layer was further extracted with 6×350 mL phosphate buffer (0.2 M, pH 6.5). The pH of the combined phosphate buffer washes was adjusted to pH 11–12 by addition of Na$_2$CO$_3$ (sat'd aqueous solution), followed by extraction with 6×500 mL CH$_2$Cl$_2$. The combined organic layers were dried over anhydrous Na$_2$SO$_4$, filtered and concentrated in vacuo to yield an oily crude product. The crude product was purified by silica gel chromatography (50 g flash grade silica gel, 0–5% MeOH/CH$_2$Cl$_2$ step gradient) to yield 2.04 g of a sticky yellow solid (23%).

TLC: Merck Silica Gel 60 plates, Rf 0.29 with 90/10 CH$_2$Cl$_2$/CH$_3$OH, see with UV (254/366) and ninhydrin stain.

HPLC: HP 1100 HPLC chromatograph, Waters 5×100 mm NovaPak HR C18 column, 0.100 mL injection, 0.75 mL/min, 1.500 mL injection loop, 280 nm detection, A=water (0.1% HFBA) and B=MeCN (0.1% HFBA), gradient 10% B 2 min, 10–80% B over 18 min, 80–100% B over 2 min, 100% B 2 min, retention time 17.0 min.

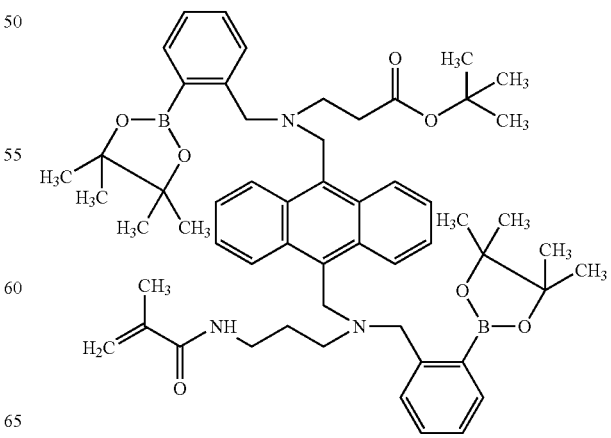

B. 9-[N-[2-(4,4,5,5,-tetramethyl-1,3,2-dioxaborolano)benzyl]-N-[3-(methacrylamido)propylamino]methyl]-10-[N-[2-(4,4,5,5,-tetramethyl-1,3,2-dioxaborolano)benzyl]-N-[2-(tert-butoxycarbonyl)ethylamino]methyl]anthracene.

A solution of 9-[N-[3-(methacrylamido)propylamino]methyl]-10-[N-[2-(tert-butoxycarbonyl)ethylamino]methyl]anthracene (1.5 g, 3.1 mmol), DIEA (3.16 g, 4.26 mL, 24.4 mmol, 7.9 equiv.), 2-bromomethylphenylboronic acid pinacol ester (3.64 g, 12.2 mmol, 3.9 equiv.) and a few crystals of BHT in 50 mL CHCl$_3$ was stirred in the dark at ambient temperature for 16 hours. At this time, the reaction mixture was concentrated and the residue suspended in 200 mL ether. The ether layer was extracted with 3×125 mL phosphate buffer (0.2 M, pH 7.0), dried over anhydrous Na$_2$SO$_4$, filtered and concentrated in vacuo to yield a crude product. The residue was triturated with hexanes to yield 2.14 g (76%) of a white solid.

HPLC: HP 1100 HPLC chromatograph, Waters 5×100 mm NovaPak HR C18 column, 0.200 mL injection, 0.75 mL/min, 1.500 mL injection loop, 280 nm detection, A=water (0.1% HFBA) and B=MeCN (0.1% HFBA), gradient 10% B 2 min, 10–80% B over 18 min, 80–100% B over 2 min, 100% B 2 min, retention time 19.2 min.

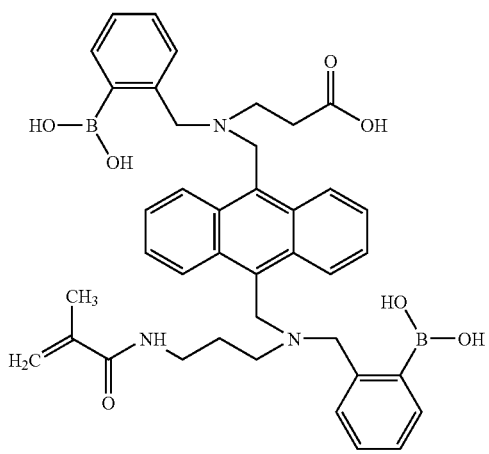

C. 9-[N-(2-boronobenzyl)-N-[3-(methacrylamido)propylamino]methyl]-10-[N-(2-boronobenzyl)-N-[2-(carboxyethyl)amino]methyl]anthracene.

A solution of 9-[N-[2-(4,4,5,5,-tetramethyl-1,3,2-dioxaborolano)benzyl]-N-[3-(methacrylamido)propylamino]methyl]-10-[N-[2-(4,4,5,5,-tetramethyl-1,3,2-dioxaborolano)benzyl]-N-[2-(tert-butoxycarbonyl)ethylamino]methyl]anthracene (0.294 g, 0.319 mmol) in 5 mL of 20% TFA/CH$_2$Cl$_2$ was stirred in the dark at ambient temperature for 22 hours. At this time, the reaction mixture was concentrated and the residue triturated with ether. The residue was dissolved in 5 mL 90:10 acetone/water and stirred for 2 hours. At this time, the reaction mixture was concentrated and the residue triturated with water and PBS (pH 7.4 containing 0.02% NaN$_3$ and 1 mM EDTA) resulting in the recovery of 0.062 g (28%) of a light yellow solid.

HPLC: HP 1100 HPLC chromatograph, Waters 5×100 mm NovaPak HR C18 column, 0.100 mL injection, 0.75 mL/min, 1.500 mL injection loop, 280 nm detection, A=water (0.1% HFBA) and B=MeCN (0.1% HFBA), gradient 10% B 2 min, 10–80% B over 18 min, 80–100% B over 2 min, 100% B 2 min, retention time 17.4 min.

FAB MS: Glycerol matrix; Calc'd for $C_{46}H_{53}B_2N_3O_7$ (bis glycerol adduct) $[M]^+$ 813. Found $[M+2]^+$ 815.

D. N,N-dimethylacrylamide hydrogel with 9-[N-(2-boronobenzyl)-N-[3-(methacrylamido)propylamino]methyl]-10-[N-(2-boronobenzyl)-N-[2-(carboxyethyl)amino]methyl]anthracene.

A solution of N,N-dimethylacrylamide (40% wt.) and N,N'-methylenebisacrylamide (0.8% wt.) in phosphate buffer, pH=7.4, 200 mM was prepared. 9-[N-(2-boronobenzyl)-N-[3-(methacrylamido)propylamino]methyl]-10-[N-(2-boronobenzyl)-N-[2-(carboxyethyl)amino]methyl]anthracene (14 mg, 2.0×10$^{-5}$ mole) and 60 mg of fructose were combined with 2 ml of MeOH. This solution was sonicated until all fructose dissolved and evaporated to yield a solid. To this solid 1 ml of phosphate buffer solution containing monomers was added. After sonication for 10 minutes this solution was filtered through 0.2 µM PTFE filter. Aqueous ammonium persulfate (20 µL, 5% wt.) was combined with the formulation. The resulting solution was placed in a glove box purged with nitrogen. An aqueous solution of N,N,N',N'-tetrametylethylenediamine (40 µL, 5% wt.) was added to the monomer formulation to accelerate polymerization. The resulted formulation was poured in a mold constructed from microscope slides and 100 µM stainless steel spacer. After being kept for 8 hours in nitrogen atmosphere the mold was placed in phosphate buffered saline (10 mM, pH=7.4), the microscope slides were separated, and the hydrogel was removed. The hydrogel was washed with 100 ml of phosphate buffered saline (PBS) containing 1 mM lauryl sulfate sodium salt and 1 mM EDTA tetrasodium salt for 3 days, the solution being changed every day, followed by washing with EtOH/PBS (20/80 by vol., 3×100 ml), and finally with PBS (pH=7.4, 3×100 ml). The resulting hydrogel film was stored in PBS (10 mM, pH=7.4) containing 0.02% wt. sodium azide and 1 mM EDTA tetrasodium salt.

II. Modulation of Fluorescence with Glucose.

Figure 15:
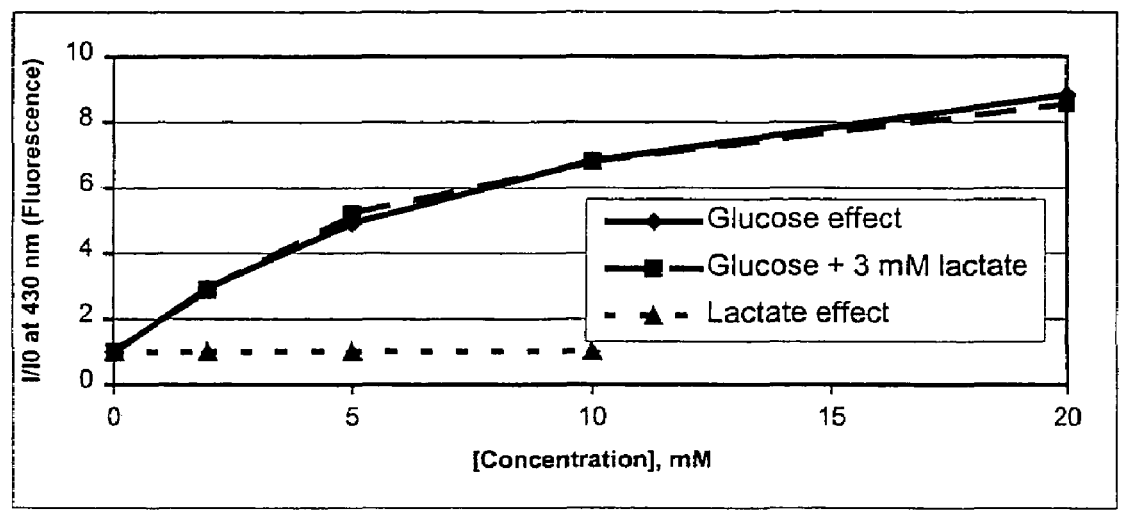
FIG. 15 shows the relative fluorescence emission (I @ 430 nm) of an indicator exposed to glucose and lactate as described in Example 12.

The modulation of the fluorescence of the 2-(carboxyethyl)amine indicator/DMA hydrogel film prepared in this example by glucose and lactate was determined. FIG. 15 shows the relative fluorescence emission (I @ 430 nm) of the hydrogel film in PBS (pH 7.4 containing 0.02% NaN$_3$ and 1 mM EDTA) containing 0 to 20 mM α-D-glucose, 0 to 10 mM L-sodium lactate, and 0–20 mM glucose in the presence of 3 mM L-sodium lactate. The hydrogel film (100 µm thickness, 8 mm diameter disk) was mounted in a PMMA cuvette at a 45° angle. All measurements were made at 37° C. in a Shimadzu RF-5301 spectrofluorometer with excitation at 370 nm (slit=3 nm) and emission at 430 nm (slit=3 nm) at low PMT sensitivity. Glucose and L-sodium lactate concentrations were checked using the YSI Model 2300 STAT plus glucose analyzer. The data is plotted as the average of triplicate values for each data point. The fluorescence was affected by the presence of glucose, but not by the presence of lactate. Moreover, the presence of lactate (4 mM) had no significant effect on the 0–20 mM glucose calibration curve.

EXAMPLE 13

Fluorescent Glucose Indicator Containing Two Detectable Moieties:

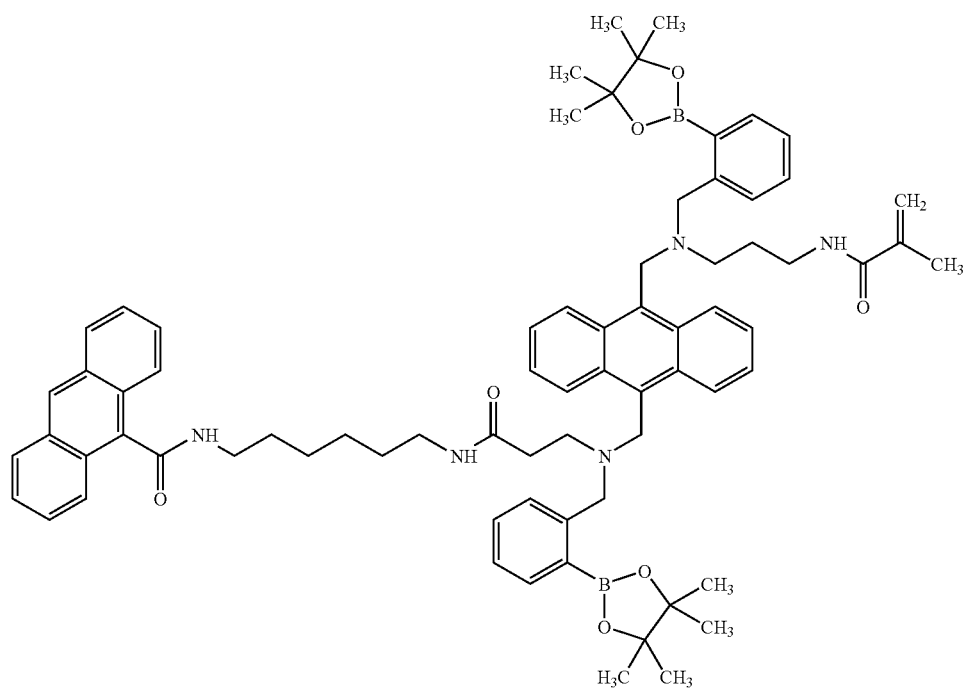

Chemical Name: 9-[N-(2-boronobenzyl)-N-[3-(methacrylamido)propylamino]methyl]-10-[N-(2-boronobenzyl)-N-[3-(N-6-(9-anthracenecarboxamido)hexylamino carbonyl)ethylamino]methyl]anthracene (uncapped)

Chemical Formula: $C_{73}H_{87}B_2N_5O_7$

MW: 1168

Physical appearance: faint yellow powder

Solubility: PBS/methanol, methanol, ethanol, chloroform, dichloromethane

Pinacol capped compound:
9-[N-[2-(4,4,5,5,-tetramethyl-1,3,2-dioxaborolano)benzyl]-N-[3-(methacrylamido)propylamino]methyl]-10-[N-[2-(4,4,5,5,-tetramethyl-1,3,2-dioxaborolano)benzyl]-N-[3-(N-6-(9-anthracenecarboxamido)hexylamino carbonylethylaminomethyl]anthracene.

I. Synthesis

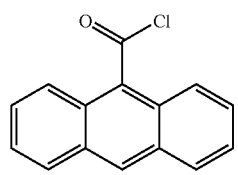

A. 9-Anthracenoyl Chloride:

Anthracene-9-carboxylic acid (1.2 g, $5.4 \times 10^{-3}$ mole) was combined with 15 ml of thionyl chloride. The solution was refluxed for 2 hours followed by evaporation of the volatile components. The obtained solid was dried under high vacuum for 24 hours yielding 1.3 g of material (quantitative yield). This material was used as is in the next step.

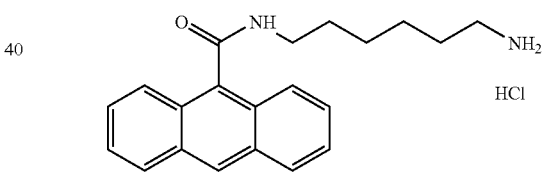

B. N-(6-Aminohexyl)-anthracene-9-carboxamide hydrochloric acid salt:

9-Anthracenoyl chloride (1.3 g, 5.4 mmole) in 50 ml of anhydrous $CH_2Cl_2$ was added dropwise to 11.6 g of hexamethylenediamine (100 mmole) in 100 ml of $CH_2Cl_2$ at 0° C. The solution was stirred at 0° C. for 1 hour then allowed to warm to room temperature and stirred overnight. The solvent was evaporated and 200 ml of water was added to the residue. This mixture was sonicated and stirred for 1 hour then filtered. The filtered solid was dried under vacuum for 24 hours. MeOH (50 ml) and 2 ml of conc. HCl was added to the solid, followed by evaporation of MeOH. The resulting solid was washed with hot $CH_2Cl_2$/MeOH (90/10 vol. %) and recrystallized from MeOH, yielding 0.51 g of the product (26%). The purity of the product was checked by HPLC.

HPLC: HP 1100 HPLC chromatograph, Waters 5×100 mm NovaPak HR C18 column, 0.1 mL injection, 0.75 mL/min flowrate, 2 mL injection loop, 280 nm detection, A=water (0.1% HFBA) and B=MeCN (0.1% HFBA), gradient 10% B 2 min, 10–80% B over 18 min, 80–100% B over 2 min, 100% B 2 min, retention time 16.5 min.

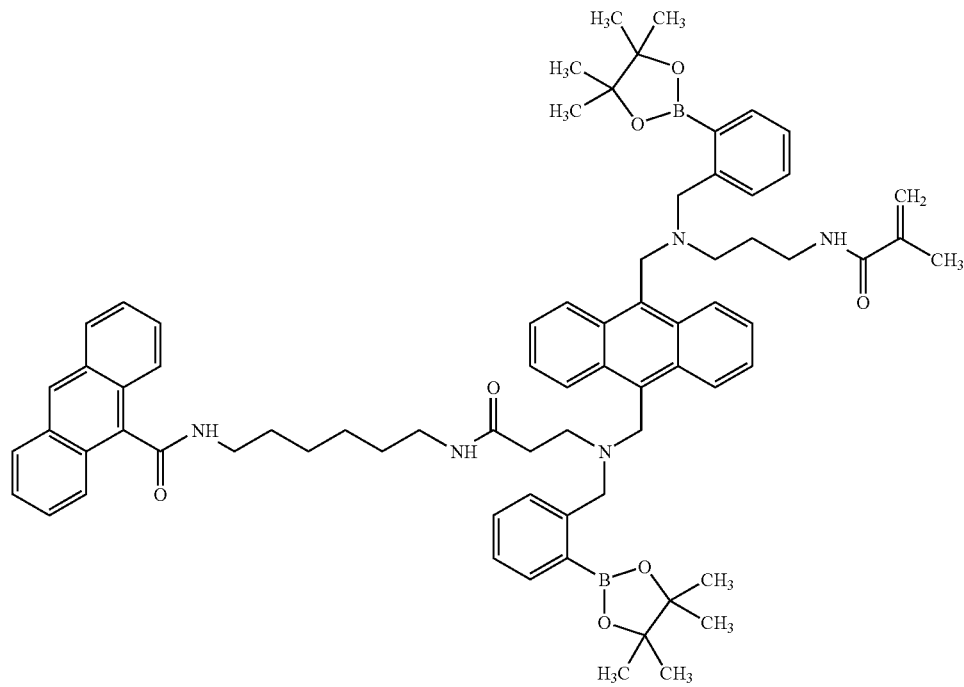

C. 9-[N-[2-(4,4,5,5,-tetramethyl-1,3,2-dioxaborolano)benzyl]-N-[3-(methacrylamido)propylamino]methyl]-10-[N-[2-(4,4,5,5,-tetramethyl-1,3,2-dioxaborolano)benzyl]-N-[3-(N-6-(9-anthracenecarboxamido)hexylamino carbonylethylaminomethyl]anthracene:

9-[N-[2-(4,4,5,5,-tetramethyl-1,3,2-dioxaborolano)benzyl]-N-[3-(methacrylamido)propylamino]methyl]-10-[N-[2-(4,4,5,5,-tetramethyl-1,3,2-dioxaborolano)benzyl]-N-[2-carboxyethylamino]methyl]anthracene (40 mg, $4.5 \times 10^{-5}$ mole) was combined with N-(6-aminohexyl)-anthracene-9-carboxamide hydrochloric acid salt (20 mg, $5.6 \times 10^{-5}$ mole), diphenylphosphoryl azide (15.4 mg, $5.6 \times 10^{-5}$ mole), and 2 ml of DMF. Diisopropylethylamine(39 20 μL, $2.44 \times 10^{-4}$ mole) was added to the mixture and the solution was stirred at room temperature for 24 hours. The DMF was evaporated under high vacuum, the residue was dissolved in 50 ml of EtOAc and washed with water (3×10 ml). The EtOAc solution was separated, dried ($Na_2SO_4$), and evaporated producing 46 mg of solid (87% yield). Purity of the material was checked by HPLC.

HPLC: HP 1100 HPLC chromatograph, Waters 5×100 mm NovaPak HR C18 column, 0.1 mL injection, 0.75 mL/min flowrate, 2 mL injection loop, 280 nm detection, A=water (0.1% HFBA) and B=MeCN (0.1% HFBA), gradient 10% B 2 min, 10–80% B over 18 min, 80–100% B over 2 min, 100% B 2 min, retention time 20.42 min.

FAB mass-spectrum, glycerol matrix: calculated for $C_{67}H_{75}B_2N_5O_9$ (bis glycerol adduct) [M]+=1116, found [M+1]+=1117.

II. Effect of Glucose on Fluorescence of Indicator Immobilized in Hydrogel Film

Preparation of HEMA/Methacrylic Acid Hydrogel with Glucose Indicator:

A 50% wt. solution of 2-hydroxyethylmethacrylate(4.75 g) and methacrylic acid (0.25 g) in phosphate buffer, pH=7.4, 200 mM was prepared. Glucose indicator (11 mg, $1.0 \times 10^{-5}$ mole) and 60 mg of fructose were combined with 2 ml of MeOH. This solution was sonicated until all fructose dissolved and evaporated to yield a solid. To this solid 1 ml of phosphate buffer solution containing monomers was added. After sonication for 10 minutes this solution was filtered through 0.2 μM PTFE filter. Aqueous ammonium persulfate (20 μL, 5% wt.) was combined with the formulation. The resulting solution was placed in a glove box purged with nitrogen. An aqueous solution of N,N,N',N'-tetramethylethylenediamine (40 μL, 5% wt.) was added to the monomer formulation to accelerate polymerization. The resulting formulation was poured in a mold constructed from microscope slides and a 100 μM stainless steel spacer. After being kept for 8 hours in a nitrogen atmosphere the mold was placed in phosphate buffered saline (10 mM, pH=7.4), the microscope slides were separated, and the hydrogel was removed. The hydrogel was washed with 100 ml of phosphate buffered saline (PBS) containing 1 mM lauryl sulfate sodium salt and 1 mM EDTA tetrasodium salt for 3 days, the solution being changed every day, followed by washing with EtOH/PBS (20/80 by vol., 3×100 ml), and finally with PBS (pH=7.4, 3×100 ml). The resulting hydrogel film was stored in PBS (10 mM, pH=7.4) containing 0.02% wt. sodium azide and 1 mM EDTA tetrasodium salt.

Effect of Glucose and L-Sodium Lactate on Hydrogel Film Containing Glucose Indicator.

The experiment was conducted in a Shimadzu RF-5301 PC spectrofluorimeter equipped with a variable temperature attachment. Excitation wavelength was set at 370 nm, slits 3/3 nm, low PMT sensitivity, emission was scanned from 400 to 600 nm. Glucose and L-sodium lactate concentrations were checked using YSI Model 2300 STAT plus glucose analyzer.

Figure 16:
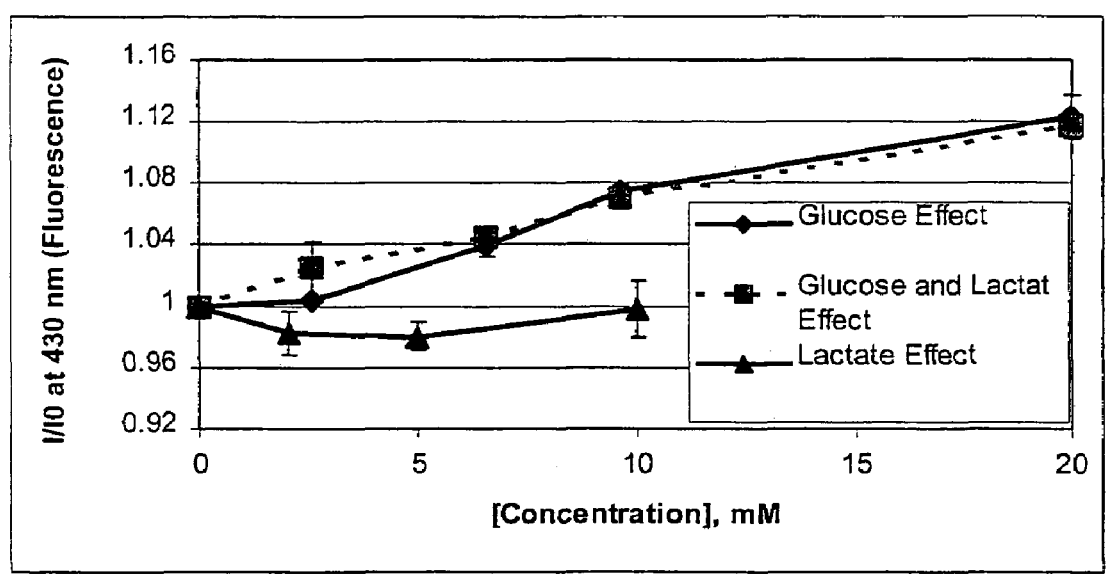
FIG. 16 illustrates the fluorescence of an indicator exposed to glucose and lactate as described in Example 13.

The hydrogel film (100 μm thickness, round shape ~8 mm diameter) was mounted in a PMMA cuvette at 45° angle. Phosphate buffered saline (PBS), pH=7.4 containing the desired amount of glucose, L-sodium lactate, and glucose with L-sodium lactate were heated to 37° C. in a water bath and placed in the PMMA cell containing the mounted hydrogel. After each addition the PMMA cell was allowed to equilibrate for 45 min at 37° C. Fluorescence intensity measurements for each glucose/lactate concentration were conducted on two different samples and an average value was used in the calibration curve. Calibration curves (Fluorescence Intensity at 430 nm vs. concentration) were obtained for glucose, L-sodium lactate, and glucose in the presence of 3 mM L-sodium lactate. The results are shown in FIG. 16.

EXAMPLE 14

6-(3-carboxypropionamido)hexylamino indicator monomer

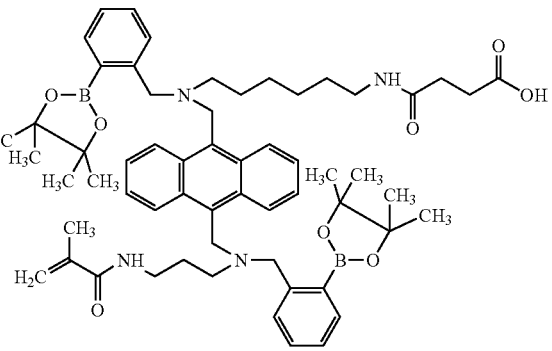

Pinacol capped compound:
   9-[N-[2-(4,4,5,5,-tetramethyl-1,3,2-dioxaborolano)benzyl]-N-[3-(methacrylamido)propylamino]methyl]-10-[N-[2-(4,4,5,5,-tetramethyl-1,3,2-dioxaborolano)benzyl]-N-[6-(3-carboxypropionamido)hexylamino]methyl]anthracene.

Uncapped compound:
   9-[N-(2-boronobenzyl)-N-[3-(methacrylamido)propylamino]methyl]-10-[N-(2-boronobenzyl)-N-[6-(3-carboxypropionamido)hexylamino]methyl]anthracene.

Synthesis:
   The synthesis may be carried out in an analogous fashion to Example 11 using 9-[N-[3-(methacrylamido)propylamino]methyl]-10-N-[6-(hexylamino)methyl]anthracene as the starting material. In contrast, the amine starting material is reacted with the N-hydroxysuccinimide (NHS) ester of the mono methyl ester of succinic acid in place of the NHS ester of cyclohexanecarboxylic acid used in Example 11. An additional base hydrolysis step is required to complete the synthesis.

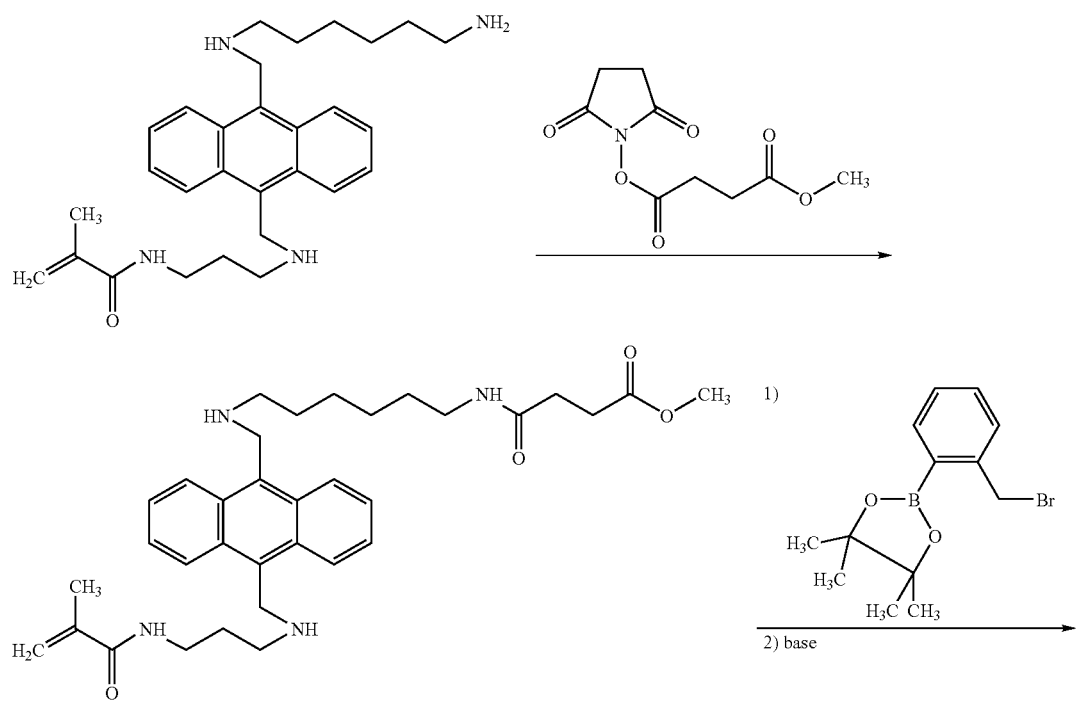

-continued
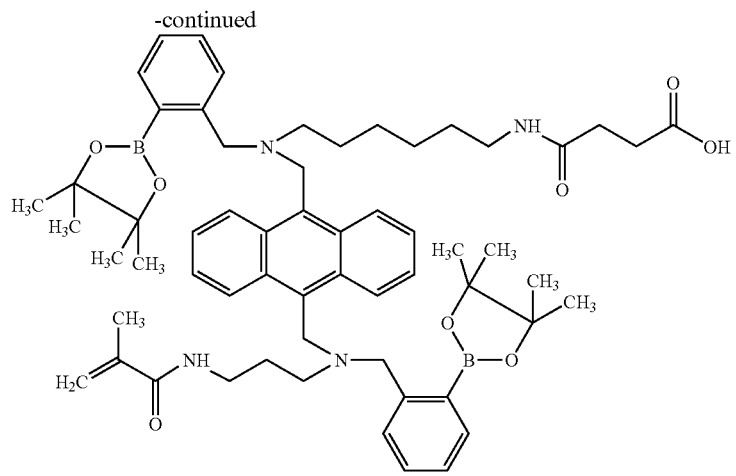
EXAMPLE 15
Glucose Indicator/Monomer Excited with Visible Light
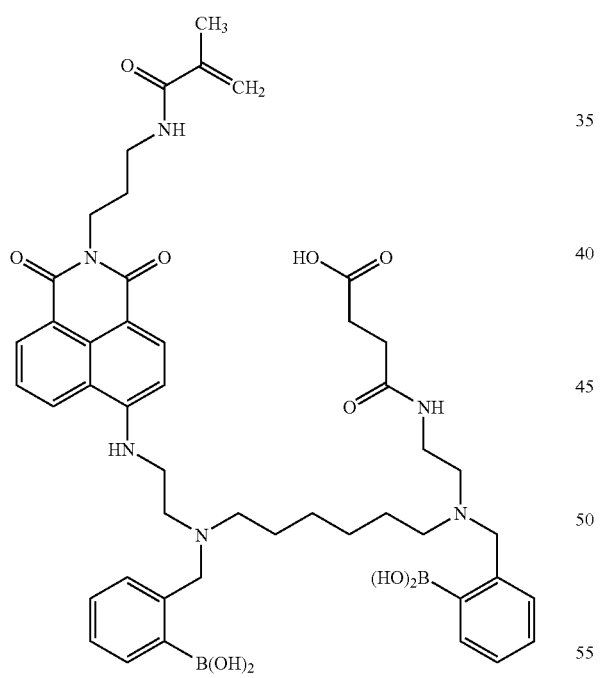
Chemical Name: N-(3-Methacrylamidopropyl)-4-[2-N-[[2-(borono)benzyl]-[6-(N-[2-(borono)benzyl]-6-N-(3-carboxypropanamidoethyl)aminohexyl]]aminoethylamino]naphthalene-1,8-dicarboximide
Chemical Formula: $C_{47}H_{60}B_2N_6O_{10}$
M. W.: 890

The compound may be synthesized as shown below:
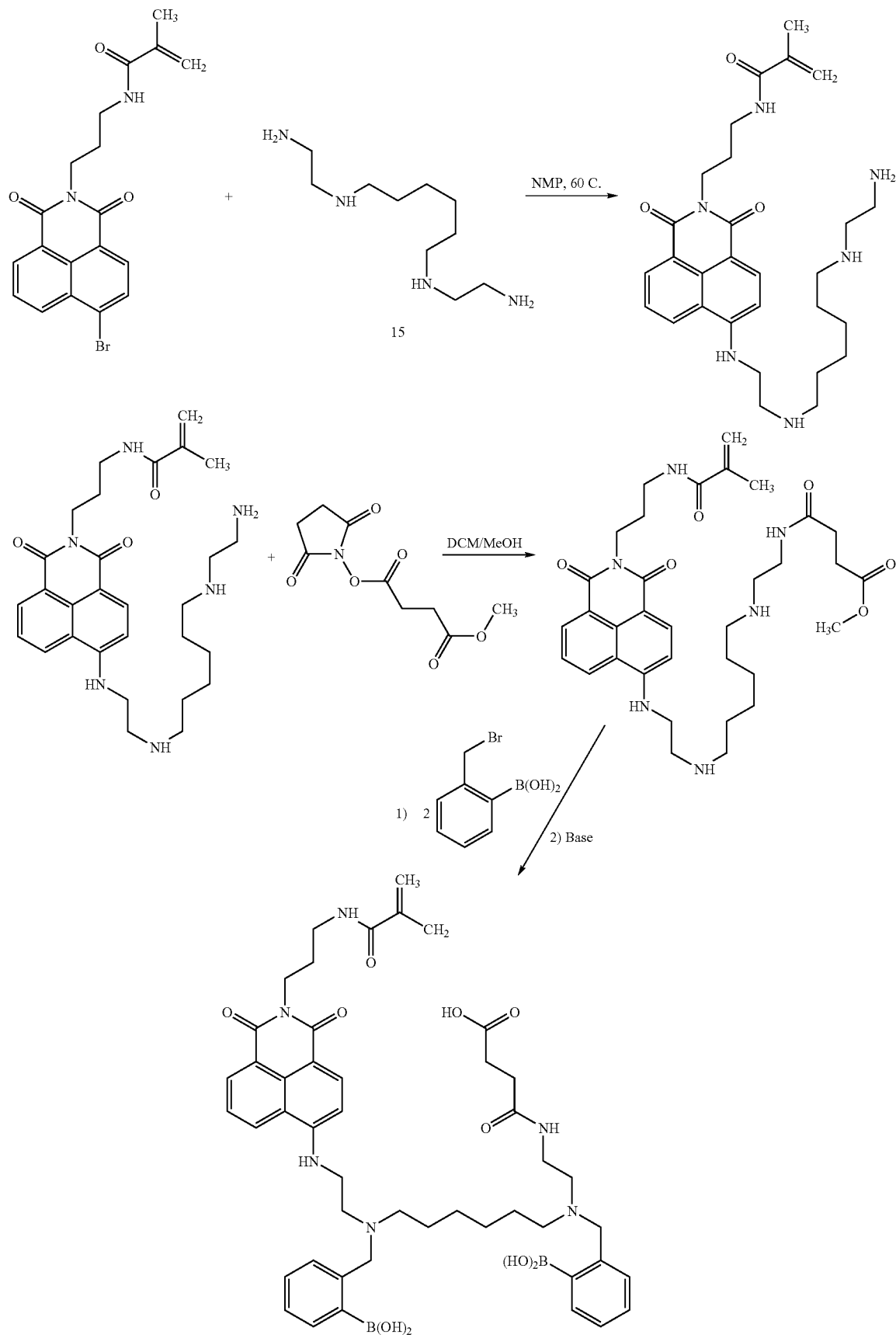

EXAMPLE 16
Alternate Glucose Indicator/Monomer Excited with Visible Light
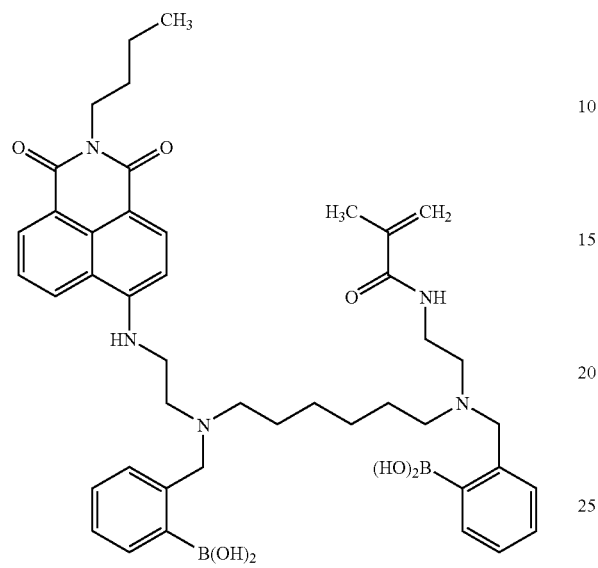
Chemical Name: N-Butyl-4-[2-N-[[2-(borono)benzyl]-[6-(N-[2-(borono)benzyl]-6-N-(2-methacrylamidoethyl)aminohexyl]]aminoethylamino]naphthale ne-1,8-dicarboximide
Chemical Formula: $C_{44}H_{57}B_2N_5O_7$
M. W.: 789.5
The compound may be synthesized as shown below:
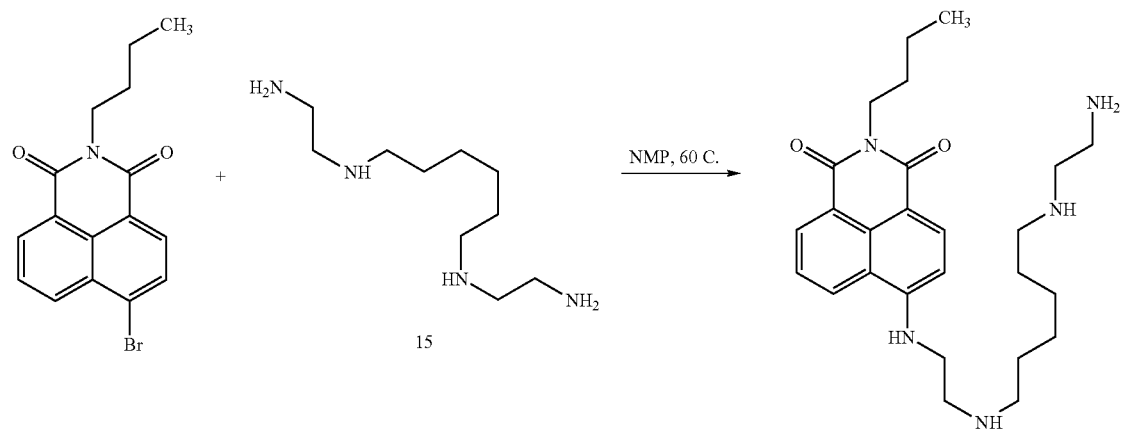

-continued

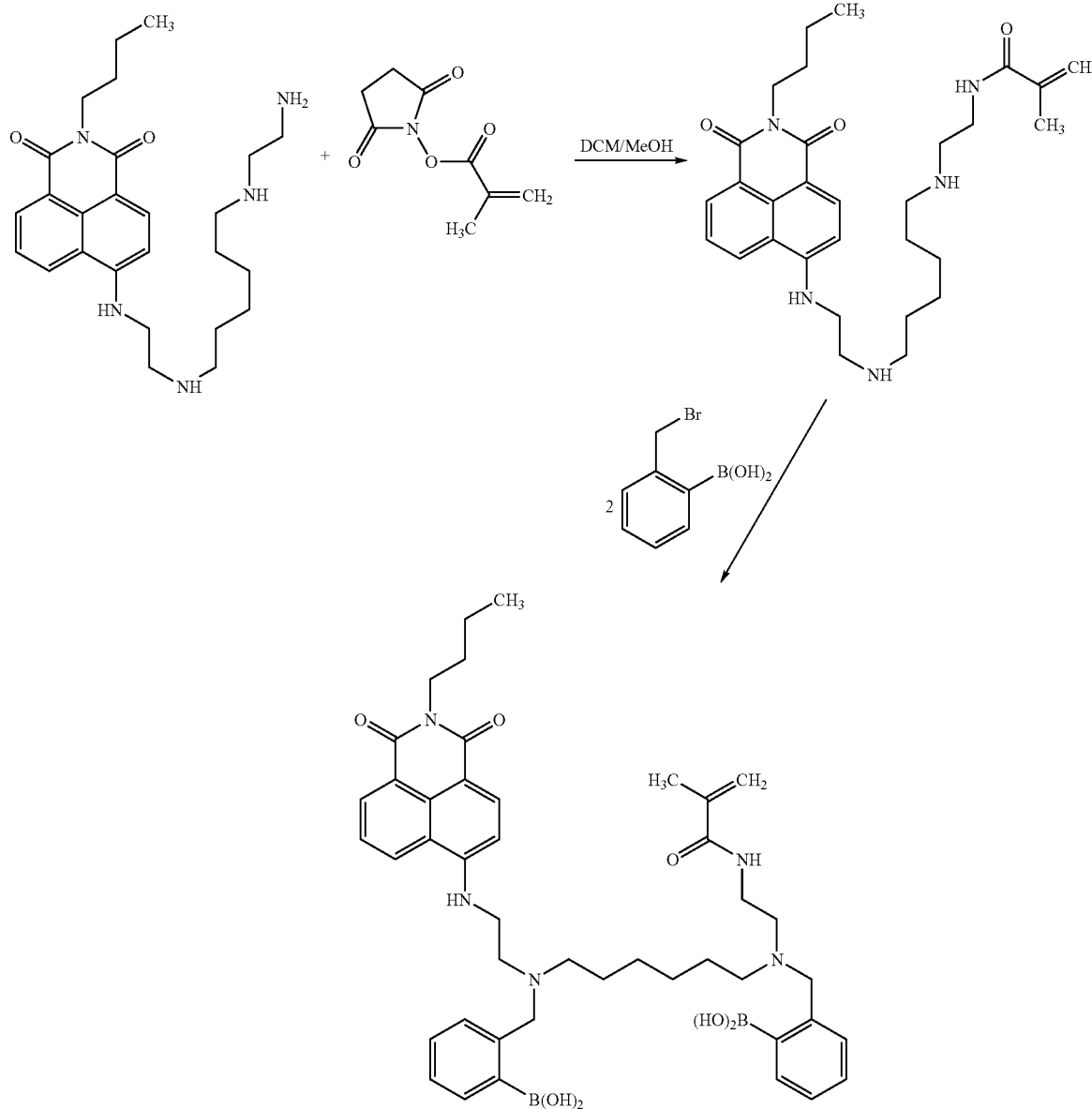

What is claimed is:
1. A compound selected from the group consisting of:
9-[N-[2-(5,5-dimethyl[1,3,2]dioxaborinan-2-yl)-benzyl]-N-[2-(2-methacroyloxyethoxy)ethylamino]methyl]-10-[N-[2-(5,5dimethyl[1,3,2]dioxaborinan-2-yl)ben-zyl]-N-[2-(2-hydroxyethoxy)ethylamino]-methyl]anthracene;
9-[N-(2-boronobenzyl)-N-[2-(2-methacroyloxyethoxy)-ethylamino]methyl]-10-[N-(2-boronobenzyl)-N-[2-(2-hydroxyethoxy)ethylamino]methyl]anthracene;
9,10-bis[N-(2boronobenzyl)-N-[2-(carboxyethyl)amino]-methyl]anthracene;
9,10-bis[N-[2-(5,5-dimethyl[1,3,2]dioxaborinan-2-yl)-benzyl]-N-[3-(methacrylamido)propylamino]methy-lanthracene;
9,10-bis[N-(2-boronobenzyl)-N-[3-(methacrylamido)-propylamino]methylanthracene;
9-[N-[2-(5,5-dimethyl[1,3,2]dioxaborinan-2-yl)-benzyl]-N-[3-(methacrylamido)propylamino]methyl]-10-[N-[2-(5,5-dimethyl[1,3,2]dioxaborinan-2-yl)benzyl]-N-[2-(2-hydroxyethoxy)-ethylamino]methyl]anthracene;
9[N-(2-boronobenzyl)-N-[3-(methacrylamido)-propy-lamino]methyl]-10-[N-(2-boronobenzyl)-N-[2-(2-hy-droxyethoxy)ethylamino]methyl]anthracene;
9,10-bis[N-[2-(5,5-dimethyl[1,3,2]dioxaborinan-2-yl)benzyl]-N-[2-(2-methacroyloxyethoxy)ethylamino]-methyl]anthracene;
9,10-bis[N-(2-boronobenzyl)-N-[2-(2-methacroyloxy-ethoxy)ethylamino]methyl]anthracene;
9,10-bis[N-(2-boronobenzyl)-N-[5-aminopentylamino]-methyl]anthracene;
9-[N-(2-boronobenzyl)-N-[3-(methacrylamido)propy-lamino]methyl]-10-[N-(2-boronobenzyl)-N-[6-(cyclo-hexanecarboxamido)hexylamino]methyl]anthracene;

9[N-[2-(4,4,5,5,-tetramethyl-1,3,2-dioxaborolano)benzyl]N-[3-(methacrylamido)propylamino]methyl]-10-[N-[2-(4,4,5,5,-tetramethyl-1,3,2-dioxaborolano)benzyl]-N-[6-(cyclohexanecarboxamido)hexylamino]methyl]anthracene;

9-[N-(2-boronobenzyl)-N-[3-(methacrylamido)propylamino]methyl]-10-[N-(2-boronobenzyl)-N-[2-(carboxyethyl)amino]methyl]anthracene;

9-[N-[2-(4,4,5,5,-tetramethyl-1,3,2-dioxaborolano)benzyl]-N-[3-(methacrylamido)propylamino]methyl]-10-[N-[2-(4,4,5,5,-tetramethyl-1,3,2-dioxaborolano)benzyl]-N-[2-(carboxyethyl)amino]methyl]anthracene;

9-[N-(2-boronobenzyl)-N-[3-(methacrylamido)propylamino]methyl]-10-[N-(2-boronobenzyl)-N-[3-(N-6-(9-anthracenecarboxamido)hexylamino carbonyl)ethylamino]methyl]anthracene;

9[N-[2-(4,4,5,5,-tetramethyl-1,3,2-dioxaborolano)benzyl]-N-[3-(methacrylamido)propylamino]methyl]-10-[N-[2-(4,4,5,5,-tetramethyl-1,3,2-dioxaborolano)benzyl]-N-[3-(N-6-(9-anthracenecarboxamido)hexylamino carbonylethylaminomethyl]anthracene;

9-[N-[2-(4,4,5,5,-tetramethyl-1,3,2-dioxaborolano)benzyl]-N-[3-(methacrylamido)propylamino]methyl]-10-[N-[2-(4,4,5,5,-tetramethyl-1,3,2-dioxaborolano)benzyl]-N-[6-(3-carboxypropionamido)hexylamino]methyl]anthracene; and 9-[N-(2-boronobenzyl)-N-[3-(methacrylamido)propylamino]methyl]-10-[N-(2-boronobenzyl)-N-[6-(3-carboxypropionamido)hexylamino]methyl]anthracene;

and salts thereof.

2. 9-[N-[3-(methacrylamido)propylamino]-methyl]-10-N-[(6-aminohexylamino)methyl]anthracene.

3. 9-[N-[3-(methacrylamido)propylamino]-methyl]-10-[N-[6-(cyclohexanecarboxamido)hexylamino]methyl]anthracene.

4. 9-[N-(2-boronobenzyl)-N-[3-(methacrylamido)-propylamino]methyl]-10-[N-(2-boronobenzyl)-N-[6-(cyclohexanecarboxamido)hexylamino]methyl]anthracene.

5. 9-[N-(2-boronobenzyl)-N-[3-(methacrylamido)-propylamino]methyl]-10-[N-(2-boronobenzyl)-N-[2-(carboxyethyl)amino]methyl]anthracene.

* * * * *